United States Patent

Itoh et al.

Patent Number: 6,069,162
Date of Patent: May 30, 2000

[54] INDOLYL AND BENZOFURANYL CARBOXAMIDES AS INHIBITORS OF NITRIC OXIDE PRODUCTION

[75] Inventors: Yoshikuni Itoh, Takatsuki; Takumi Yatabe, deceased, late of Tsukuba, by Yoshiko Yatabe, legal representative; Takayuki Inoue; Hitoshi Hamashima, both of Tsukuba, all of Japan

[73] Assignee: Fujisawa Pharmaceutical Co., Ltd., Osaka, Japan

[21] Appl. No.: 09/147,317

[22] PCT Filed: May 22, 1997

[86] PCT No.: PCT/JP97/01757

§ 371 Date: May 28, 1999

§ 102(e) Date: May 28, 1999

[87] PCT Pub. No.: WO97/45425

PCT Pub. Date: Dec. 4, 1997

[30] Foreign Application Priority Data

May 27, 1996 [AU] Australia .................................. PO0084
Dec. 16, 1996 [AU] Australia .................................. PO4219

[51] Int. Cl.[7] .................. A61K 31/4178; A61K 31/427; C07D 403/12; C07D 405/12; C07D 417/12
[52] U.S. Cl. .......................... 514/397; 514/314; 546/167; 548/311.4; 548/312.1; 548/181; 548/201; 548/204
[58] Field of Search .............................. 548/311.4, 312.1; 546/167; 514/314, 397

[56] References Cited

U.S. PATENT DOCUMENTS 5,102,901  4/1992  Van Wijngaarden et al. .......... 514/397

FOREIGN PATENT DOCUMENTS

95/27490  10/1995  WIPO .

*Primary Examiner*—Laura L. Stockton

*Attorney, Agent, or Firm*—Oblon, Spivak, McClelland, Maier & Neustadt, P.C.

[57] ABSTRACT

The object amide compounds of the present invention are novel and can be represented by the following general formula (I):

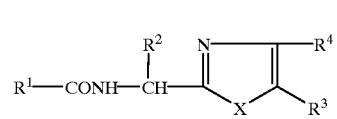

(I)

wherein
$R^1$ is indolyl or benzofuranyl;
$R^2$ is hydrogen, lower alkylthio(lower)alkyl or a group of the formula:

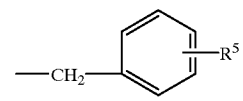

in which $R^5$ is hydrogen, lower alkoxy or halogen;
$R^3$ is hydrogen, quinolyl or phenyl which may have a suitable substituent selected from the group consisting of lower alkyl, lower alkoxy, lower alkylthio and halogen;
$R^4$ is hydrogen or optionally esterified carboxy; and
X is S or $NR^6$
in which $R^6$ is hydrogen, lower alkyl or a group of the formula:

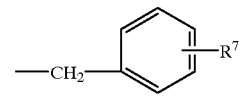

in which $R^7$ is lower alkyl or lower alkoxy.

16 Claims, No Drawings

INDOLYL AND BENZOFURANYL CARBOXAMIDES AS INHIBITORS OF NITRIC OXIDE PRODUCTION

This application is a 371 of PCT/JP97/01757 filed May 22, 1997.

BACKGROUND OF THE INVENTION

1. Field of the Invention

This invention relates to new amide compounds and pharmaceutically acceptable salts thereof which are useful as medicament.

2. Description of the Background

Some peptide compounds have been known as described, for example, in EP 0 394 989 A2.

SUMMARY OF THE INVENTION

This invention relates to new amide compounds.

DETAILED DESCRIPTION OF THE PREFERRED EMBODIMENTS

One object of this invention is to provide the new and useful amide compounds and pharmaceutically acceptable salts thereof which possess a strong inhibitory activity on the production of nitric oxide (NO).

Another object of this invention is to provide a process for the preparation of the amide compounds and salts thereof.

A further object of this invention is to provide a pharmaceutical composition comprising said amide compound or a pharmaceutically acceptable salt thereof.

Still further object of this invention is to provide a use of said amide compounds or pharmaceutically acceptable salts thereof as a medicament for prophylactic and therapeutic treatment of NO-mediated diseases such as adult respiratory distress syndrome, cardiovascular ischemia, myocarditis, heart failure, synovitis, shock (e.g., septic shock, etc.), diabetes (e.g., insulin-dependent diabetes mellitus, etc.), diabetic nephropathy, diabetic retinopathy, diabetic neuropathy, glomerulonephritis, peptic ulcer, inflammatory bowel disease (e.g., ulcerative colitis, chronic colitis, etc.), cerebral infarction, cerebral ischemia, cerebral hemorrhage, migraine, rheumatoid arthritis, gout, neuritis, postherpetic neuralgia, osteoarthritis, osteoporosis, systemic lupus erythematosus, rejection by organ transplantation, asthma, metastasis, Alzheimer's disease, arthritis, CNS disorders, and the like in human being and animals.

The object amide compounds of the present invention are novel and can be represented by the following general formula (I)

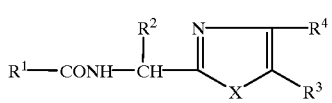

(I)

wherein

R$^1$ is indolyl or benzofuranyl;

R$^2$ is hydrogen, lower alkylthio(lower)alkyl or a group of the formula:

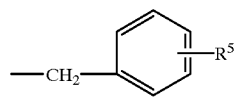

in which R$^5$ is hydrogen, lower alkoxy or halogen;

R$^3$ is hydrogen, quinolyl or phenyl which may have a suitable substituent selected from the group consisting of lower alkyl, lower alkoxy, lower alkylthio and halogen;

R$^4$ is hydrogen or optionally esterified carboxy; and

X is S or NR$^6$ in which R$^6$ is hydrogen, lower alkyl or a group of the formula:

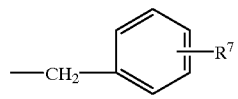

in which R$^7$ is lower alkyl or lower alkoxy.

Suitable pharmaceutically acceptable salts of the object compound (I) are conventional non-toxic salts and include, for example, a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.); an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, citrate, fumarate, methanesulfonate, benzenesulfonate, toluenesulfonate, etc.); and a salt with a basic or acidic amino acid (e.g., arginine, aspartic acid, gultamic acid, etc.).

In the above and subsequent descriptions of the present specification, suitable examples and illustration of the various definitions which the present invention intends to include within the scope thereof are explained in detail as follows.

The term "lower" is used to intend a group having 1 to 6, preferably 1 to 4, carbon atom(s), unless otherwise provided.

Suitable "lower alkyl" and "lower alkyl moiety" in the terms "lower alkylthio" and "lower alkylthio(lower)alkyl" include straight or branched one having 1 to 6 carbon atom(s), such as methyl, ethyl, propyl, isopropyl, butyl, isobutyl, sec-butyl, tert-butyl, pentyl, tert-pentyl and hexyl, and in which more preferred one is C$_1$–C$_4$ alkyl.

Suitable "lower alkoxy" includes, for example, methoxy, ethoxy, propoxy, isopropoxy, butoxy, isobutoxy, tert-butoxy, pentyloxy, tert-pentyloxy and hexyloxy, and in which more preferred one is C$_1$–C$_4$ alkoxy.

Suitable "halogen" includes, for example, fluorine, bromine, chlorine and iodine.

"Optionally esterified carboxy" includes carboxy and esterified carboxy. Suitable examples of said ester include lower alkyl ester (e.g., methyl ester, ethyl ester, propyl ester, isopropyl ester, butyl ester, isobutyl ester, tert-butyl ester, pentyl ester, tert-pentyl ester, hexyl ester, etc.); lower alkenyl ester (e.g., vinyl ester, allyl ester, etc.); lower alkynyl ester (e.g., ethynyl ester, propynyl ester, etc.); lower alkoxy (lower)alkyl ester (e.g., methoxymethyl ester, ethoxymethyl ester, isopropoxymethyl ester, 1-methoxyethyl ester, 1-ethoxyethyl ester, etc.); mono(or di or tri)-aryl(lower)alkyl ester, for example, mono(or di or tri)phenyl(lower)alkyl ester which may have one or more suitable substituent(s) [e.g., benzyl ester, 4-methoxybenzyl ester, 4-nitrobenzyl ester, phenethyl ester, trityl ester, benzhydryl ester, bis (methoxyphenyl)methyl ester, 3,4-dimethoxybenzyl ester, 4-hydroxy-3,5-di-tert-butylbenzyl ester, etc.]; and aryl ester which may have one or more suitable substituent(s) such as substituted or unsubstituted phenyl ester (e.g., phenyl ester, tolyl ester, tert-butylphenyl ester, xylyl ester, mesityl ester, cumenyl ester, 4-chlorophenyl ester, 4-methoxyphenyl ester, etc.).

The object compound (I) of the present invention can be prepared by the following process.

Process (1)

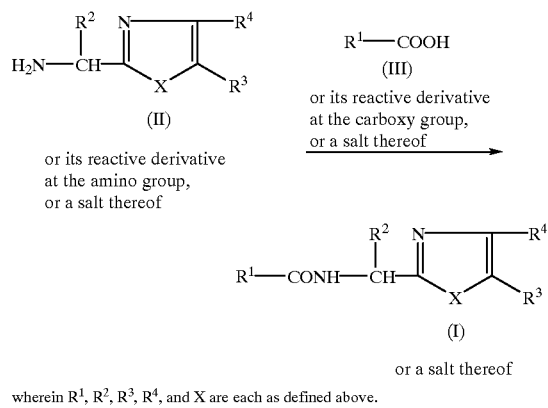

wherein $R^1$, $R^2$, $R^3$, $R^4$, and X are each as defined above.

The starting compounds can be prepared by the method of Preparation mentioned below or by a process known in the art for preparing structually analogous compounds thereto.

The process for preparing the object compound is explained in detail in the following.

Process (1)

The compound (I) or a salt thereof can be prepared by reacting the compound (II) or its reactive derivative at the amino group, or a salt thereof with the compound (III) or its reactive derivative at the carboxy group, or a salt thereof.

Suitable reactive derivative of the compound (II) includes Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as N,O-bis(trimethylsilyl) acetamide, N-trimethylsilylacetamide or the like; a derivative formed by the reaction of the compound (II) with phosphorus trichloride or phosgene.

Suitable reactive derivative of the compound (III) includes an acid halide, an acid anhydride and an activated ester. The suitable example may be an acid chloride; an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.); aromatic carboxylic acid (e.g., benzoic acid, etc.); a symmetrical acid anhydride; an activated amide with imidazole, 4-substituted imidazole, dimethylpyrazole, triazole or tetrazole; an activated ester (e.g., cyanomethyl ester, methoxymethyl ester, dimethyliminomethyl [$(CH_3)_2N^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.); or an ester with an N-hydroxy compound (e.g., N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.). These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely affect the reaction, or the mixture thereof.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diisopropylcarbodiimide; N-ethyl-N'-(3-dimethylaminopropyl)carbodiimide; N,N-carbonyl-bis-(2-methylimidazole); pentamethyleneketene-N-cyclohexylimine; diphenylketene-N-cyclohexylimine; ethoxyacetylene; 1-alkoxy-1-chloroethylene; trialkyl phosphite; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an organic or inorganic base such as an alkali metal bicarbonate, tri(lower)alkylamine, pyridine, N-(lower) alkylmorpholine, N,N-di(lower)alkylbenzylamine, or the like.

The reaction temperature is not critical, and the reaction is usually carried out under cooling to heating.

Suitable salts of the starting compounds and their reactive derivatives in Process (1) can be referred to the ones as exemplified for the compound (I).

The compounds obtained by the above process can be isolated and purified by a conventional method such as pulverization, recrystallization, column chromatography, reprecipitation, or the like.

It is to be noted that the compound (I) and the other compounds may include one or more stereoisomer(s) such as optical isomer(s) and geometrical isomer(s) due to asymmetric carbon atom(s) and double bond(s), and all of such isomers and mixtures thereof are included within the scope of this invention.

The object compounds (I) and pharmaceutically acceptable salts thereof include solvates [e.g., enclosure compounds (e.g., hydrate, etc.)].

The object compounds (I) and pharmaceutically acceptable salts thereof possess a strong inhibitory activity on the production of nitric oxide (NO).

Accordingly, the object compounds (I) and pharmaceutically acceptable salts thereof are expected to possess a nitric oxide synthase (NOS)-inhibitory activity or a NOS-production inhibitory activity.

Accordingly, they are useful for prevention and/or treatment of NO-mediated diseases such as adult respiratory distress syndrome, cardiovascular ischemia, myocarditis, heart failure, synovitis, shock (e.g., septic shock, etc.), diabetes (e.g., insulin-dependent diabetes mellitus, etc.), diabetic nephropathy, diabetic retinopathy, diabetic neuropathy, glomerulonephritis, peptic ulcer, inflammatory bowel disease (e.g., ulcerative colitis, chronic colitis, etc.), cerebral infarction, cerebral ischemia, cerebral hemorrhage, migraine, rheumatoid arthritis, gout, neuritis, postherpetic neuralgia, osteoarthritis, osteoporosis, systemic lupus erythematosis, rejection by organ transplantation, asthma, metastasis, Alzheimer's disease, arthritis, CNS disorders, and the like in human being and animals.

In order to illustrate the usefulness of the object compound (I), the pharmacological test result of the representative compound of the compound (I) is shown in the following.

Test Compound

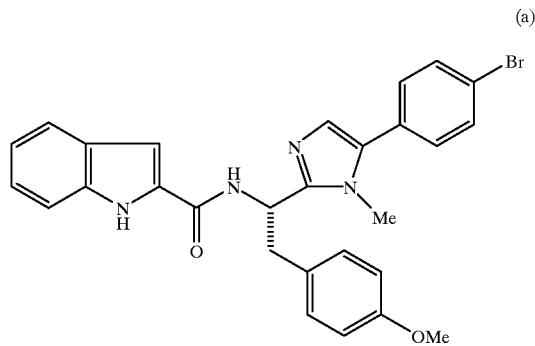

(a)

Test Assay for Inhibitory Activity on the Production of Nitric Oxide

The murine macrophage cell line RAW264.7 (American Type Culture Collection, No. TIB71) was used in this study. RAW264.7 cells were grown on F75 plastic culture flasks at 37° C., 5% in Dulbecco's modified Eagle's medium (DMEM) supplemented with L-glutamine, penicillin, streptomycin and 10% heat-inactivated fetal bovine serum. They were removed from culture flasks by rubber cell scraper and were centrifuged and resuspended in DMEM without phenol red. They were plated in 96-well microtiter plates ($10^5$ cells per well) and allowed to adhere over 2 hours. The test samples were added and the cells were preincubated for 1 hour. Thereafter the cells were activated with both of lipopolysaccharide (LPS) (1 μg/ml) and interferon γ (INF γ) (3 u/ml) for 18–24 hours. An equal volume of Griess reagent (1% sulfanilamide/0.1% N-naphthylethylenediamine dihydrochloride/2.5% $H_3PO_4$) was added and the cells were incubated at room temperature for 10 minutes. The absorbance was read at 570 nm using microplate reader and $NO_2^-$ was measured using $NaNO_2$ as a standard.

Test result

| Test compound ($10^{-5}$M) | Inhibition (%) |
|---|---|
| (a) | 100 |

For therapeutic administration, the object compound (I) of the present invention and pharmaceutically acceptable salts thereof are used in the form of a conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as granule, capsule, tablet, dragee or suppository, or in a liquid form such as solution, suspension or emulsion for injection, intravenous drip, ingestion, eye drop, etc. If needed, there may be included in the above preparation auxiliary substance such as stabilizing agent, wetting or emulsifying agent, buffer or any other commonly used additives.

The effective ingredient may usually be administered in a unit dose of 0.001 mg/kg to 500 mg/kg, preferably 0.01 mg/kg to 10 mg/kg, 1 to 4 times a day. However, the above dosage may be increased or decreased according to age, body weight and conditions of the patient or administering method.

The following Preparations and Examples are given for the purpose of illustrating the present invention in detail.

In the following Examples and Preparations, there are employed the other abbreviations in addition to the abbreviations adopted by the IUPAC-IUB (Commission on Biological Nomenclature).

The abbreviations used are as follows.
Boc: t-butoxycarbonyl
Et: ethyl
Me: methyl
Ph: phenyl
Ts: p-toluenesulfonyl The starting compounds used and the object compounds obtained in the following Preparations and Examples are given in the Tables as below, in which the formulae of the starting compounds are in the upper and the formulae of the object compounds are in the lower, respectively.

TABLE

| Preparation No. | Formula |
|---|---|
| 1 | BocNH–CH₂–COOH |
|  | BocNH–CH₂–C(O)–NH–CH₂–C(O)–Ph |
| 2 | BocNH–CH₂–C(O)–NH–CH₂–C(O)–Ph |

TABLE-continued
| Preparation No. | Formula |
|---|---|
| 3 | 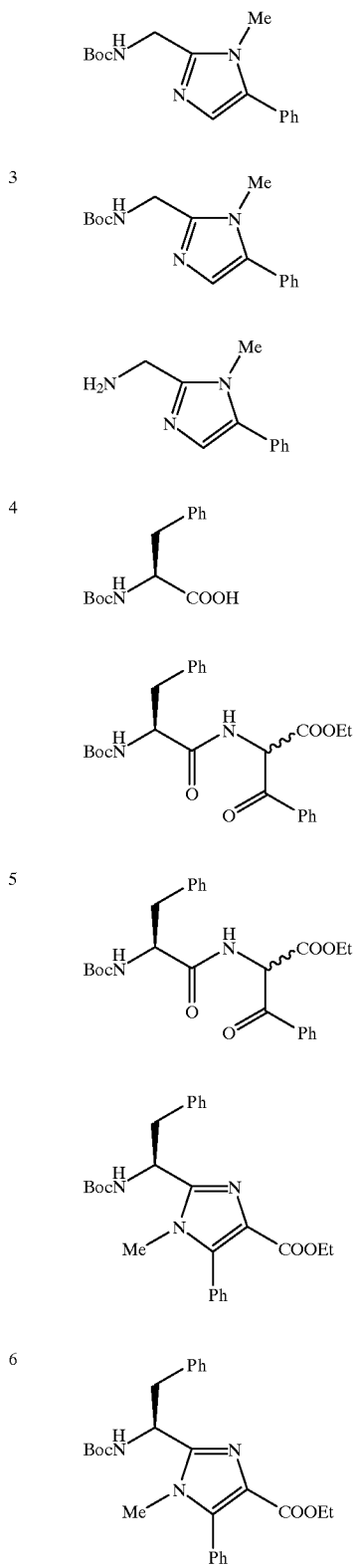 |
| 4 | |
| 5 | |
| 6 | |
TABLE-continued
| Preparation No. | Formula |
|---|---|
| | 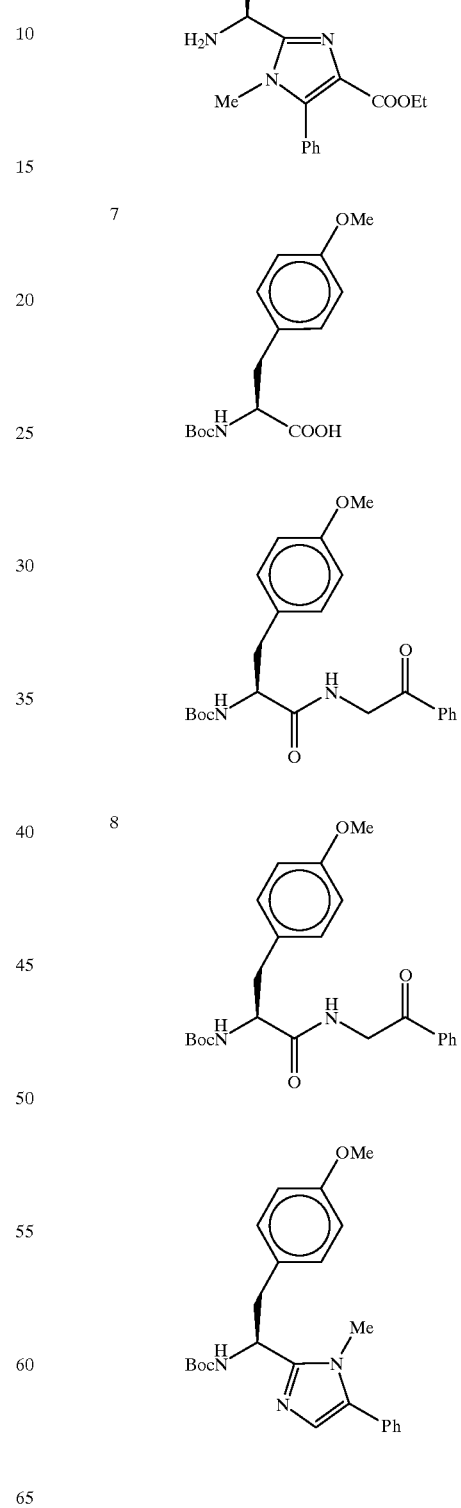 |
| 7 | |
| 8 | |

TABLE-continued
| Preparation No. | Formula |
|---|---|
| 9 | 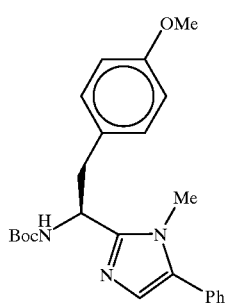 |
|  | 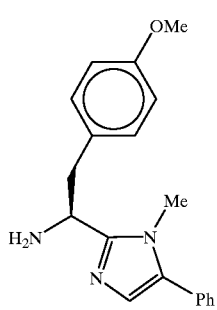 |
| 10 | 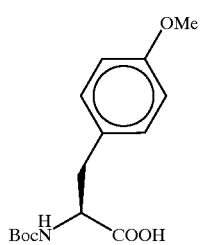 |
|  | 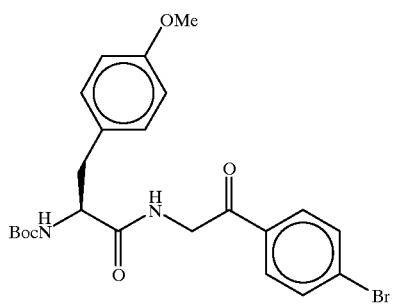 |
| 11 | 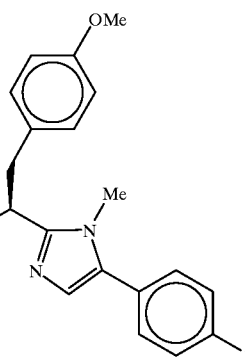 |
TABLE-continued
| Preparation No. | Formula |
|---|---|
|  | 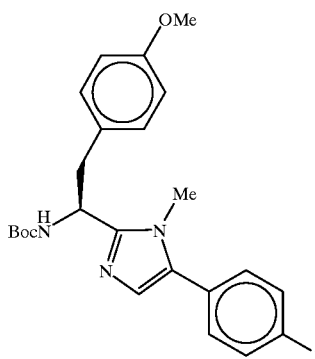 |
| 12 | 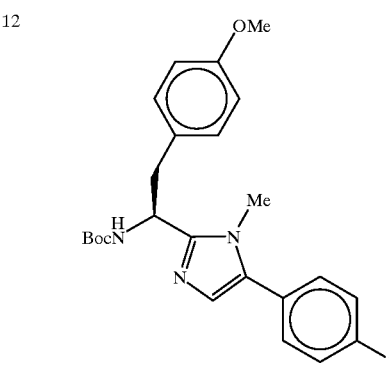 |
|  | 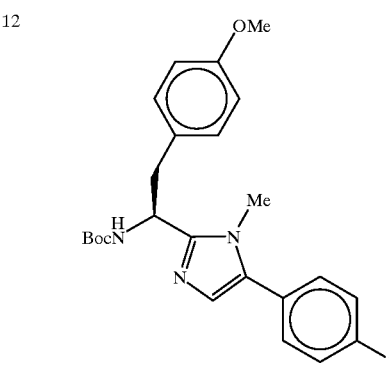 |
|  | 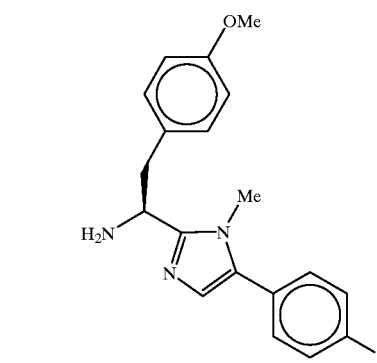 |
| 13 | 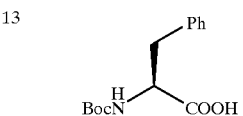 |
|  | 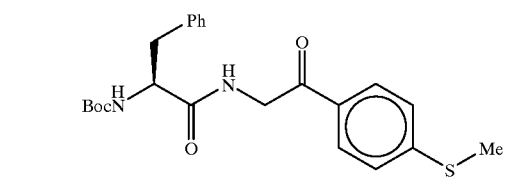 |

TABLE-continued
| Preparation No. | Formula |
|---|---|
| 14 | 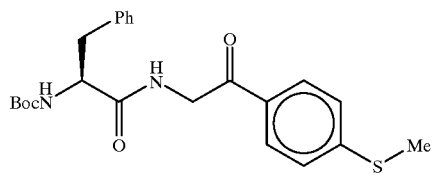 |
| 15 | 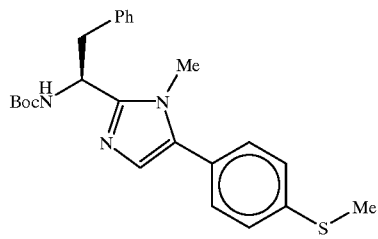 |
| 16 | 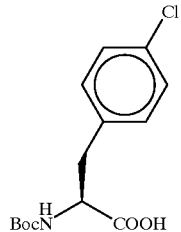 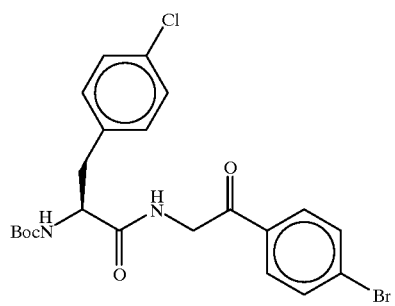 |
| 17 | 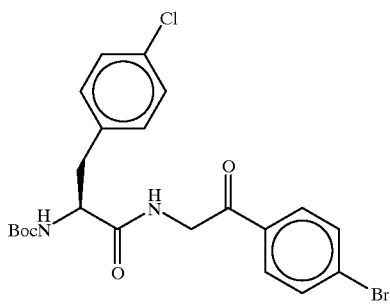 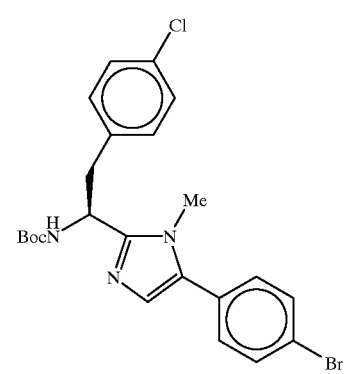 |
| 18 | 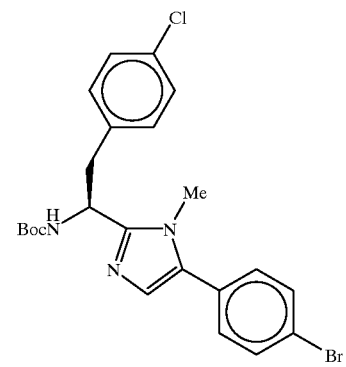 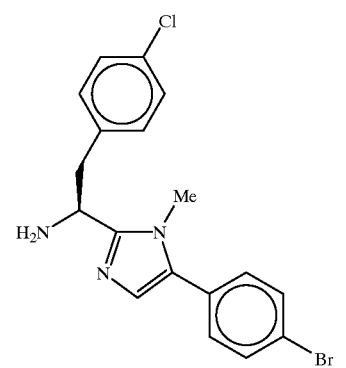 |

TABLE-continued

| Preparation No. | Formula |
|---|---|
| 19 | H₂N-CH₂-C(=O)-C₆H₄-Br ·HCl |
| 20 | Boc-NH-CH(CH₂Ph)-C(=O)-NH-CH₂-C(=O)-C₆H₄-Br |
| 20 | Boc-NH-CH(CH₂Ph)-C(=O)-NH-CH₂-C(=O)-C₆H₄-Br |
| 21 | Boc-NH-CH(CH₂Ph)-[1-Me-imidazol-2-yl]-5-(4-Br-C₆H₄) |
| 21 | Boc-NH-CH(CH₂Ph)-[1-Me-imidazol-2-yl]-5-(4-Br-C₆H₄) |
| | H₂N-CH(CH₂Ph)-[1-Me-imidazol-2-yl]-5-(4-Br-C₆H₄) |
| 22 | H₂N-CH₂-C(=O)-C₆H₄-Cl ·HCl |

TABLE-continued

| Preparation No. | Formula |
|---|---|
| 23 | Boc-NH-CH(CH₂Ph)-C(=O)-NH-CH₂-C(=O)-C₆H₄-Cl |
| 23 | Boc-NH-CH(CH₂Ph)-C(=O)-NH-CH₂-C(=O)-C₆H₄-Cl |
| | Boc-NH-CH(CH₂Ph)-[1-Me-imidazol-2-yl]-5-(4-Cl-C₆H₄) |
| 24 | Boc-NH-CH(CH₂Ph)-[1-Me-imidazol-2-yl]-5-(4-Cl-C₆H₄) |
| | H₂N-CH(CH₂Ph)-[1-Me-imidazol-2-yl]-5-(4-Cl-C₆H₄) |
| 25 | H₂N-CH₂-C(=O)-C₆H₄-Me |
| | Boc-NH-CH(CH₂Ph)-C(=O)-NH-CH₂-C(=O)-C₆H₄-Me |

TABLE-continued
| Preparation No. | Formula |
|---|---|
| 26 | 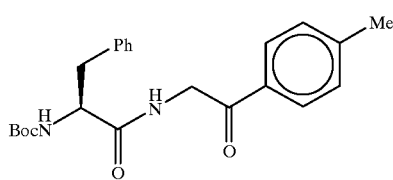 |
| 27 | 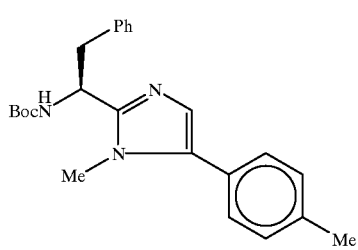 |
|  | 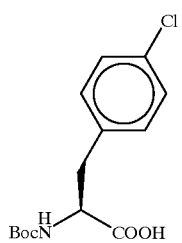 |
| 28 | 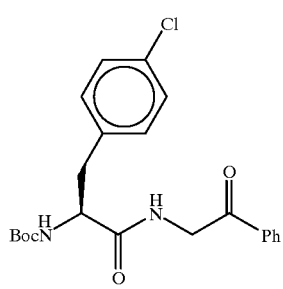 |
TABLE-continued
| Preparation No. | Formula |
|---|---|
| 29 | 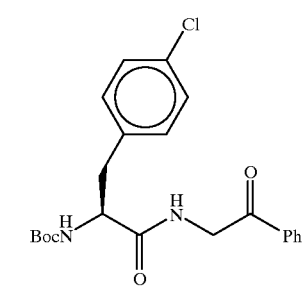 |
|  | 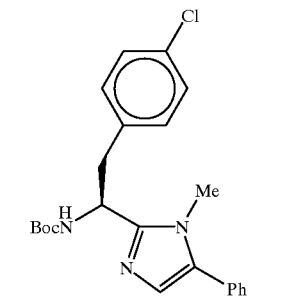 |
| 30 | 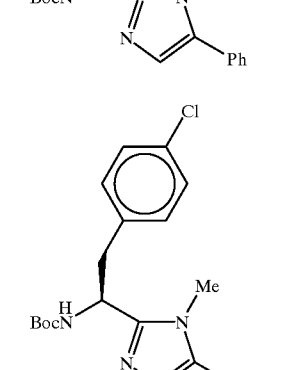 |
|  | 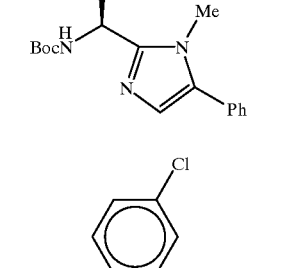 |
|  | 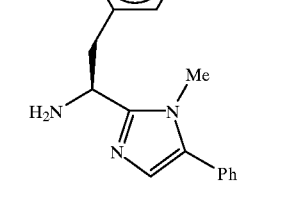 |
| 31 | 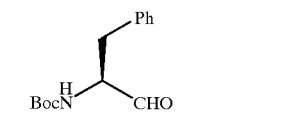 |
|  | 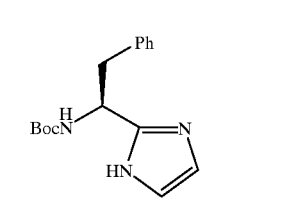 |

TABLE-continued

| Preparation No. | Formula |
|---|---|
| 32 | [structure: BocNH-CH(CH2Ph)-imidazole (NH)] |
|  | [structure: BocNH-CH(CH2Ph)-imidazole N-CH2-C6H4-Me] |
| 33 | [structure: BocNH-CH(CH2Ph)-imidazole N-CH2-C6H4-Me] |
|  | [structure: H2N-CH(CH2Ph)-imidazole N-CH2-C6H4-Me] |
| 34 | [structure: BocNH-CH(CH2Ph)-COOH] |
|  | [structure: BocNH-CH(CH2Ph)-C(O)-NH-CH2-C(O)-Ph] |
| 35 | [structure: BocNH-CH(CH2Ph)-C(O)-NH-CH2-C(O)-Ph] |
|  | [structure: BocNH-CH(CH2Ph)-(1-Me-5-Ph-imidazol-2-yl)] |
| 36 | [structure: BocNH-CH(CH2Ph)-(1-Me-5-Ph-imidazol-2-yl)] |
|  | [structure: H2N-CH(CH2Ph)-(1-Me-5-Ph-imidazol-2-yl)] |
| 37 | [structure: BocNH-CH(CH2Ph)-imidazole (NH)] |
|  | [structure: BocNH-CH(CH2Ph)-(1-Me-imidazol-2-yl)] |
| 38 | [structure: BocNH-CH(CH2Ph)-(1-Me-imidazol-2-yl)] |
|  | [structure: H2N-CH(CH2Ph)-(1-Me-imidazol-2-yl)] |

TABLE-continued
| Preparation No. | Formula |
|---|---|
| 39 | 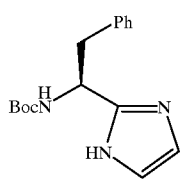 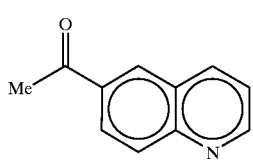 |
| 40 | 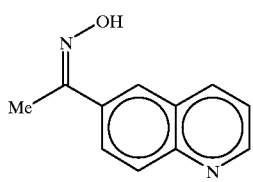 |
| 41 | 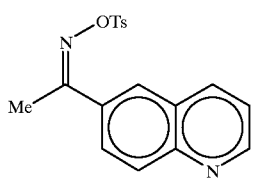 |
| 42 | 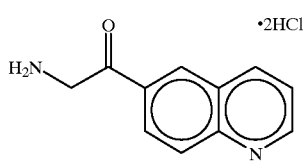 |
TABLE-continued
| Preparation No. | Formula |
|---|---|
| 43 | 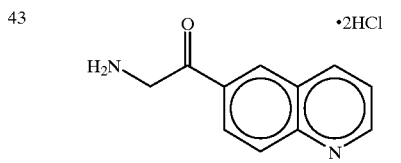 |
| | 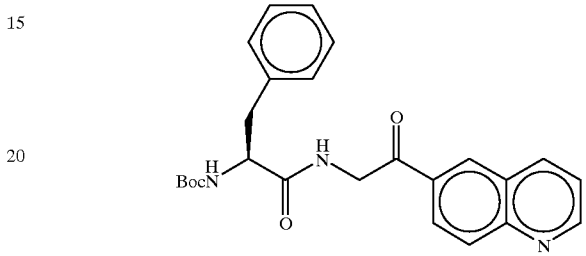 |
| 44 | 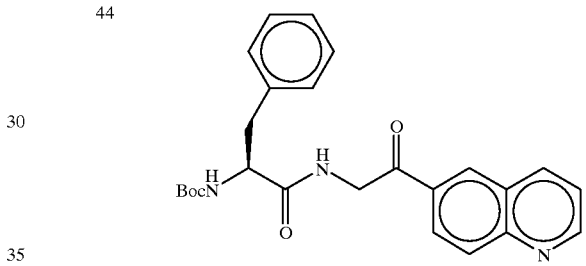 |
| | 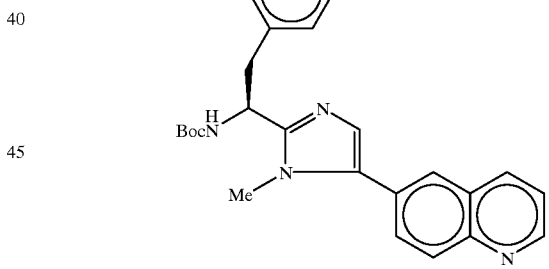 |
| 45 | 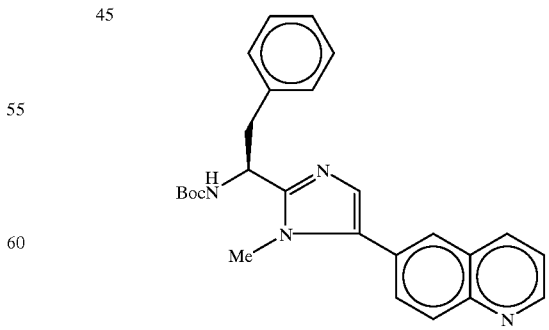 |

TABLE-continued

| Preparation No. | Formula |
|---|---|
| 46 | 3-acetylquinoline |
| 47 | (E)-quinolin-3-yl methyl ketone oxime |
| 48 | quinolin-3-yl methyl ketone O-tosyl oxime |
| 49 | 2-amino-1-(quinolin-3-yl)ethanone hydrochloride |
| | 2-(phenethylamine)-imidazole-quinoline derivative (top of page 21) |
| 50 | Boc-Phe-NH-CH₂-C(O)-quinolin-6-yl |
| | Boc-Phe-NH-CH₂-C(O)-quinolin-6-yl |
| | Boc-NH-CH(CH₂Ph)-(1-methyl-5-(quinolin-3-yl)imidazol-2-yl) |
| 51 | Boc-NH-CH(CH₂Ph)-(1-methyl-5-(quinolin-3-yl)imidazol-2-yl) |

TABLE-continued
| Preparation No. | Formula |
|---|---|
| 52 | 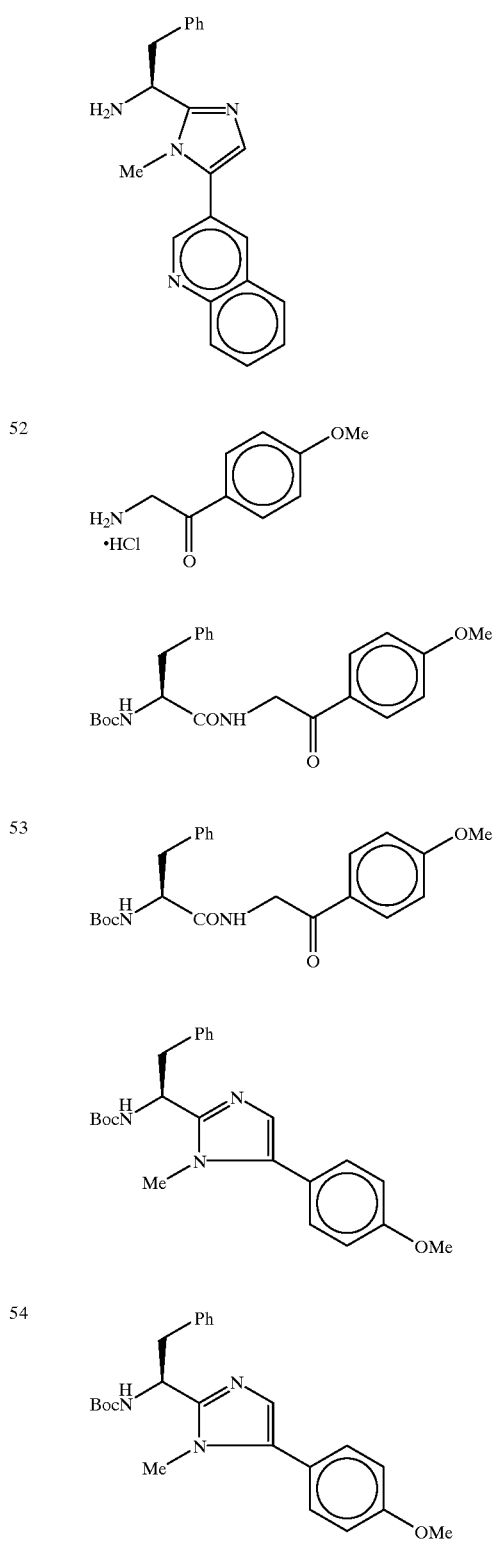 |
| 53 | |
| 54 | |
TABLE-continued
| Preparation No. | Formula |
|---|---|
| | 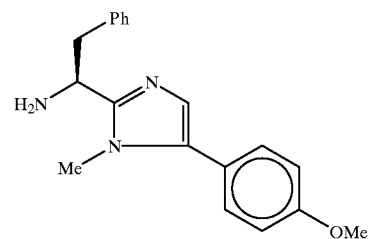 |
| 55 | 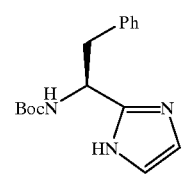 |
| | 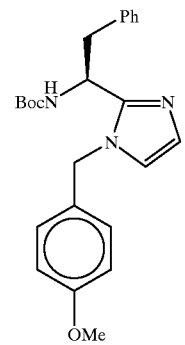 |
| 56 | 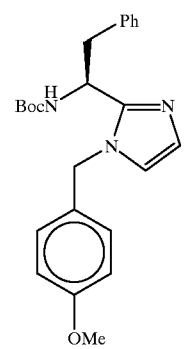 |
| | 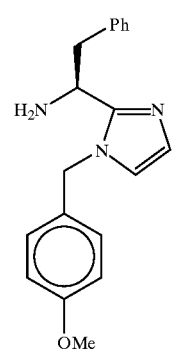 |

TABLE-continued
| Preparation No. | Formula |
|---|---|
| 57 | 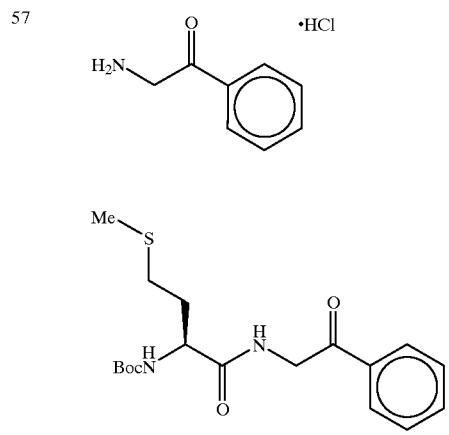 |
| 58 | 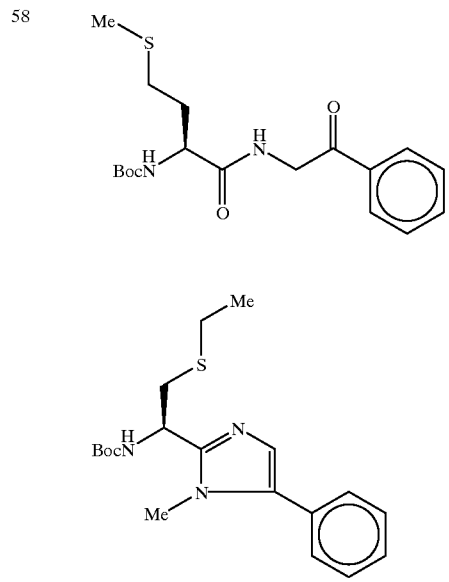 |
| 59 | |
TABLE-continued
| Preparation No. | Formula |
|---|---|
| 60 | 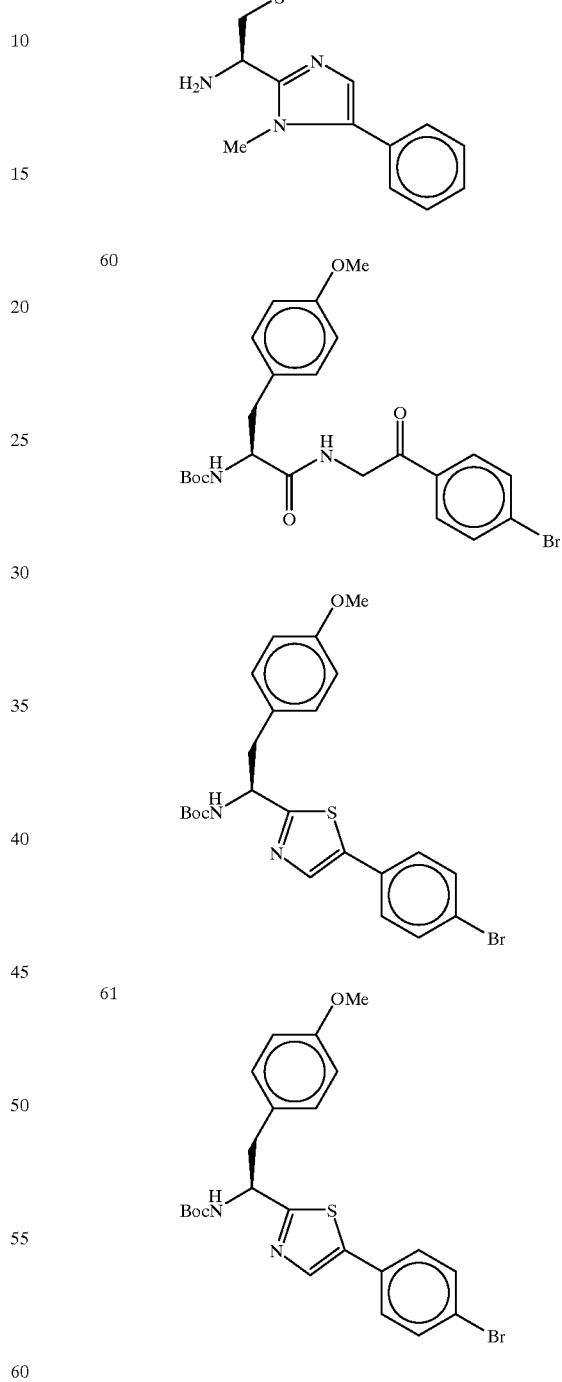 |
| 61 | |

TABLE-continued

| Preparation No. | Formula |
|---|---|
| 62 | (structure: 4-OMe-benzyl, H2N, thiazole with 4-Br-phenyl) |
| | (structure: H2N-CH2-C(=O)-4-OEt-phenyl · HCl) |
| 63 | (structure: BocNH-CH(CH2Ph)-CONH-CH2-C(=O)-4-OEt-phenyl) |
| | (structure: BocNH-CH(CH2Ph)-CONH-CH2-C(=O)-4-OEt-phenyl) |
| 64 | (structure: BocNH-CH(CH2Ph)-pyrazole(Me)-4-OEt-phenyl) |
| | (structure: BocNH-CH(CH2Ph)-pyrazole(Me)-4-OEt-phenyl) |
| | (structure: H2N-CH(CH2Ph)-pyrazole(Me)-4-OEt-phenyl) |
| 65 | (structure: H2N-CH2-C(=O)-4-Et-phenyl · HCl) |
| | (structure: BocNH-CH(CH2Ph)-CONH-CH2-C(=O)-4-Et-phenyl) |
| 66 | (structure: BocNH-CH(CH2Ph)-CONH-CH2-C(=O)-4-Et-phenyl) |
| | (structure: BocNH-CH(CH2Ph)-imidazole(NMe)-4-Et-phenyl) |
| 67 | (structure: BocNH-CH(CH2Ph)-imidazole(NMe)-4-Et-phenyl) |
| | (structure: H2N-CH(CH2Ph)-imidazole(NMe)-4-Et-phenyl) |

TABLE-continued
| Preparation No. | Formula |
|---|---|
| 68 | 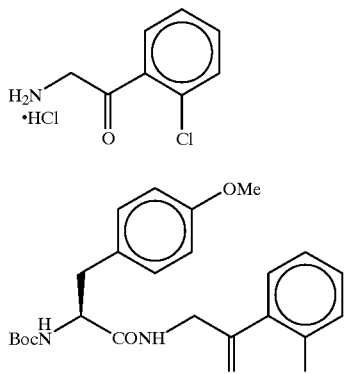 |
| 69 | 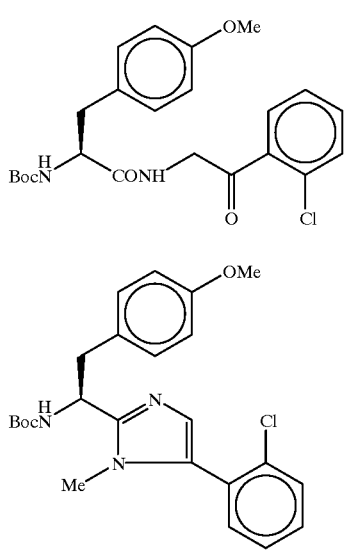 |
| 70 | 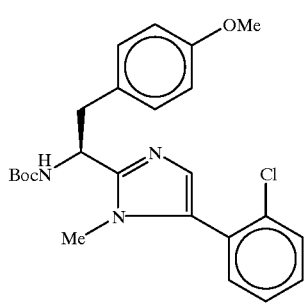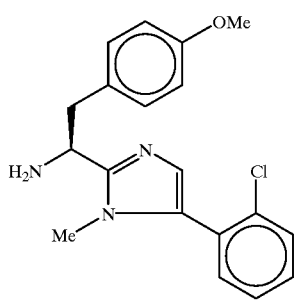 |
| 71 | 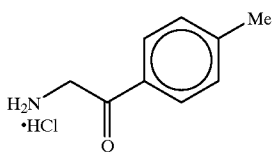 |
| 72 | 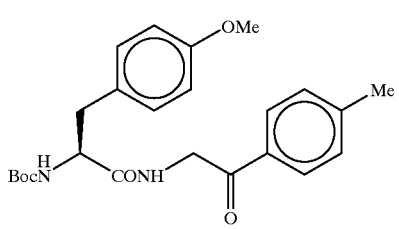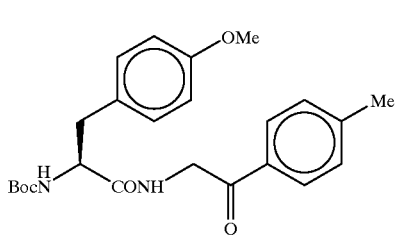 |
| 73 | 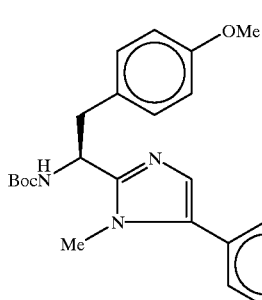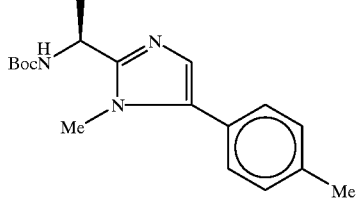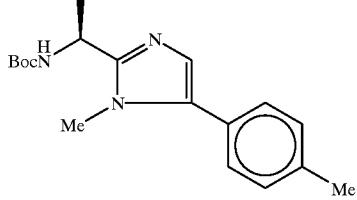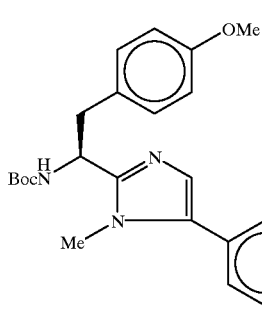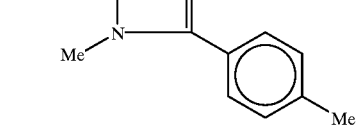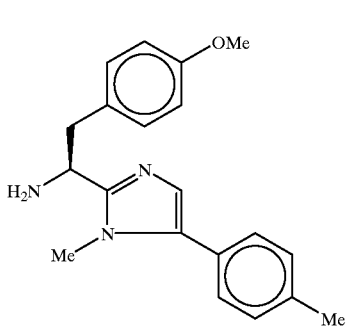 |

6,069,162
TABLE-continued
| Preparation No. | Formula |
|---|---|
| 74 | 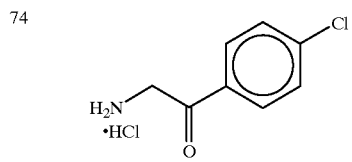 |
| | 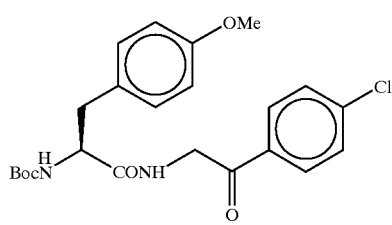 |
| 75 | 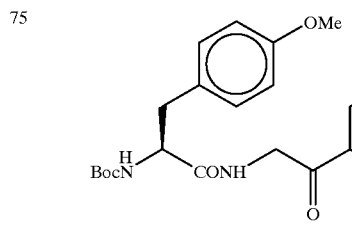 |
| | 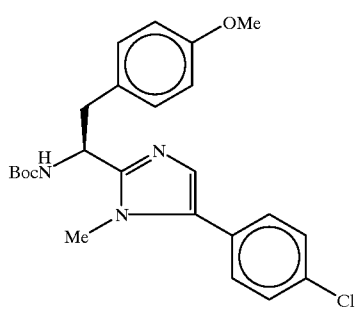 |
| 76 | 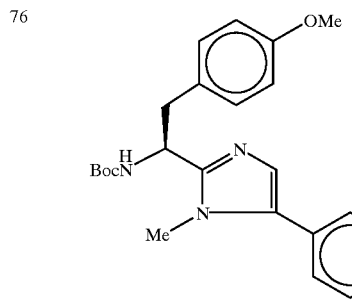 |
TABLE-continued
| Preparation No. | Formula |
|---|---|
| | 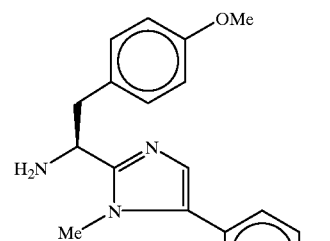 |
| 77 |  |
| | 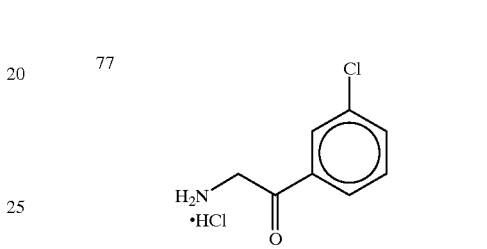 |
| 78 | 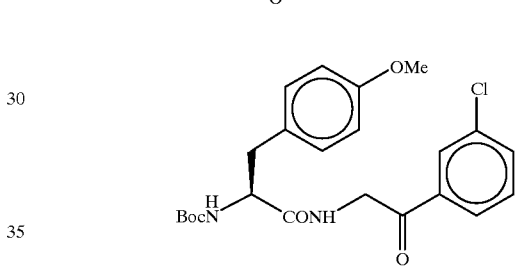 |
| | 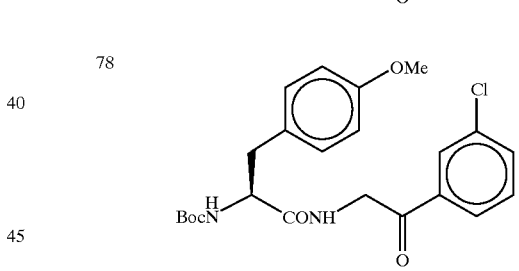 |

TABLE-continued

| Preparation No. | Formula |
|---|---|
| 79 | (structure: Boc-NH-CH(CH2-C6H4-OMe)-[1-methyl-5-(3-chlorophenyl)imidazol-2-yl]) |
| | (structure: H2N-CH(CH2-C6H4-OMe)-[1-methyl-5-(3-chlorophenyl)imidazol-2-yl]) |
| 80 | (structure: H2N-CH2-C(=O)-C6H4-F · HCl) |
| | (structure: Boc-NH-CH(CH2-C6H4-OMe)-C(=O)-NH-CH2-C(=O)-C6H4-F) |
| 81 | (structure: Boc-NH-CH(CH2-C6H4-OMe)-C(=O)-NH-CH2-C(=O)-C6H4-F) |
| | (structure: Boc-NH-CH(CH2-C6H4-OMe)-[1-methyl-5-(4-fluorophenyl)imidazol-2-yl]) |
| 82 | (structure: Boc-NH-CH(CH2-C6H4-OMe)-[1-methyl-5-(4-fluorophenyl)imidazol-2-yl]) |
| | (structure: H2N-CH(CH2-C6H4-OMe)-[1-methyl-5-(4-fluorophenyl)imidazol-2-yl]) |
| 83 | (structure: H2N-CH2-C(=O)-C6H4-OEt · HCl) |
| | (structure: Boc-NH-CH(CH2-C6H4-OMe)-C(=O)-NH-CH2-C(=O)-C6H4-OEt) |
| 84 | (structure: Boc-NH-CH(CH2-C6H4-OMe)-C(=O)-NH-CH2-C(=O)-C6H4-OEt) |
| | (structure: Boc-NH-CH(CH2-C6H4-OMe)-[1-methyl-5-(4-ethoxyphenyl)imidazol-2-yl]) |

TABLE-continued
| Preparation No. | Formula |
|---|---|
| 85 | 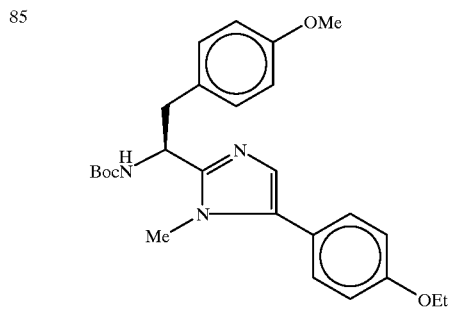<br>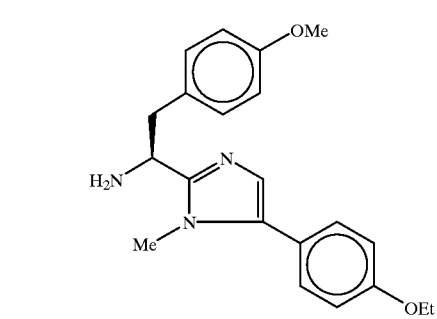 |
| 86 | 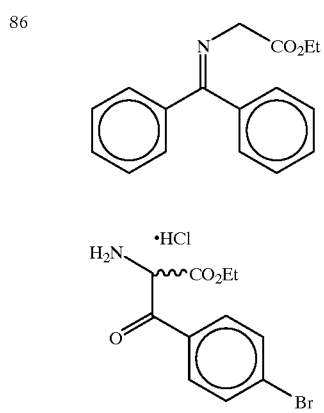 |
| 87 | 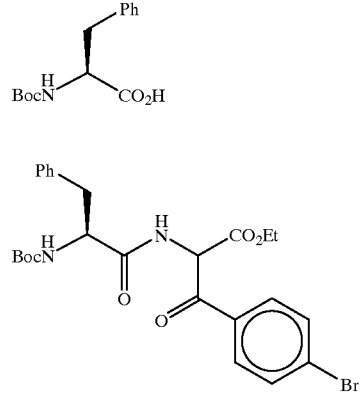 |
| 88 | 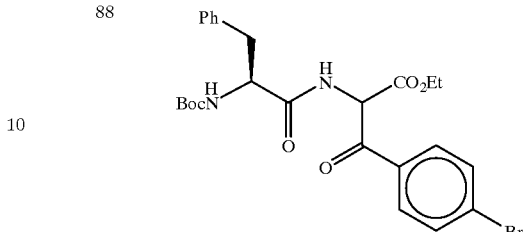<br>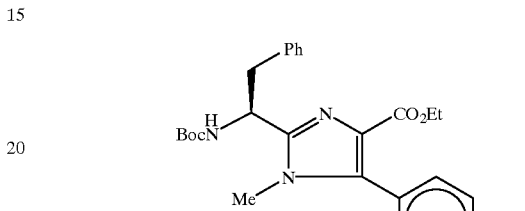 |
| 89 | 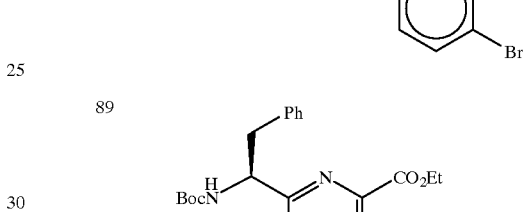<br>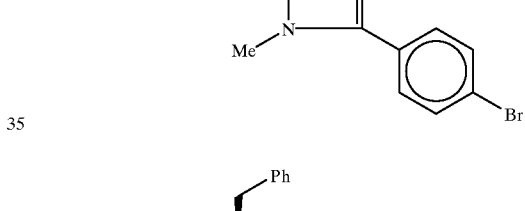 |
| 90 | 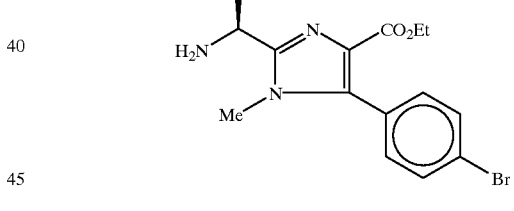<br>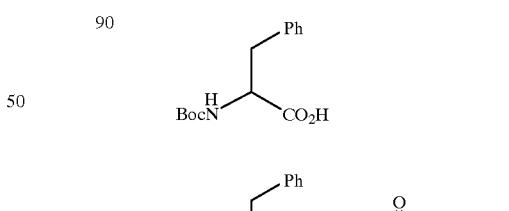 |
| 91 | 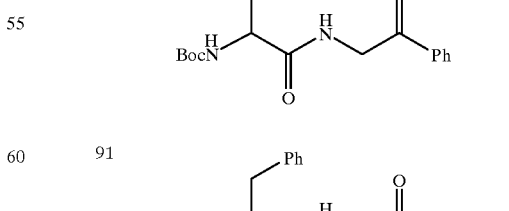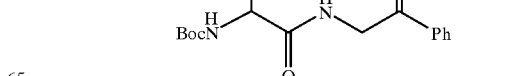 |

TABLE-continued
| Preparation No. | Formula |
|---|---|
| | 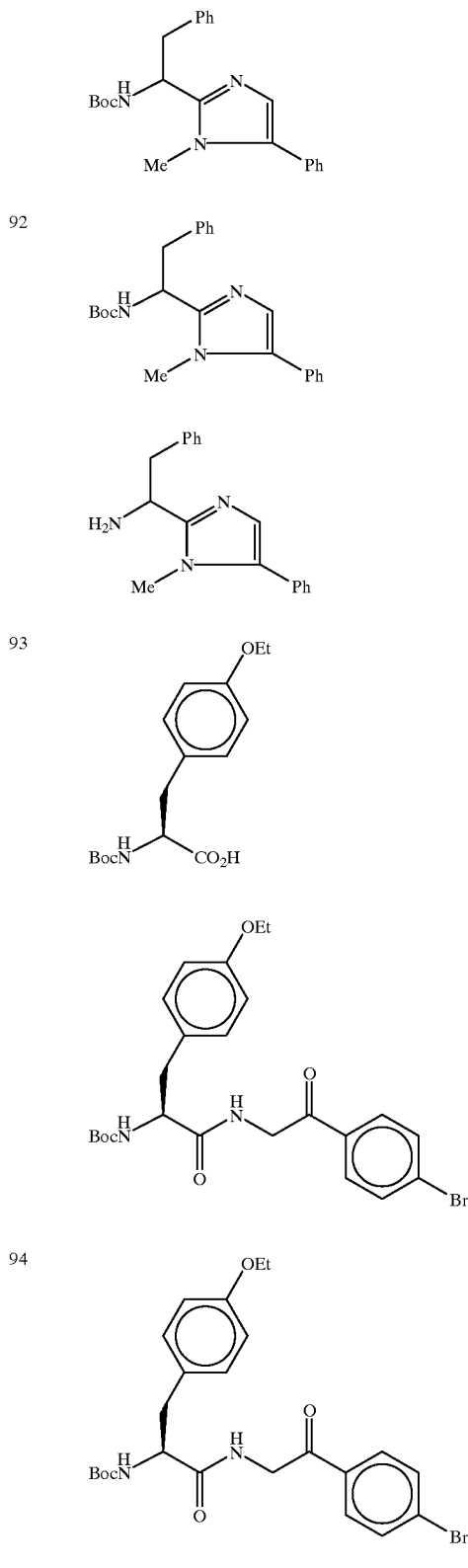 |
| 92 | |
| 93 | |
| 94 | |
TABLE-continued
| Preparation No. | Formula |
|---|---|
| | 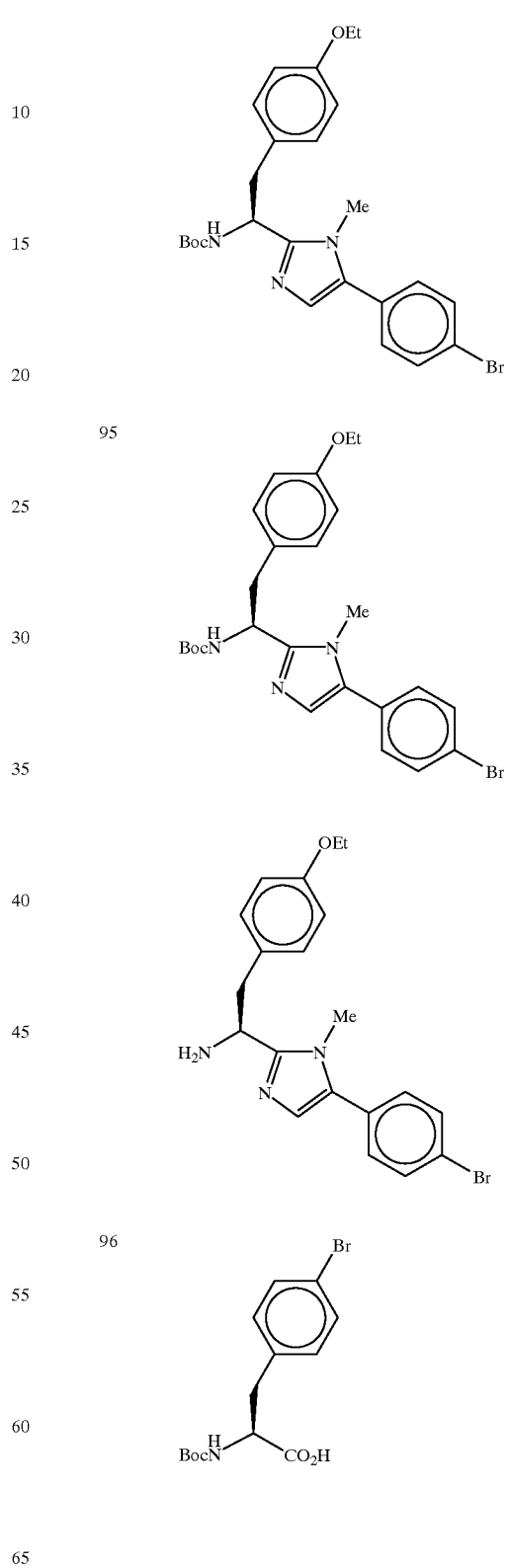 |
| 95 | |
| 96 | |

TABLE-continued
| Preparation No. | Formula |
|---|---|
| 97 | 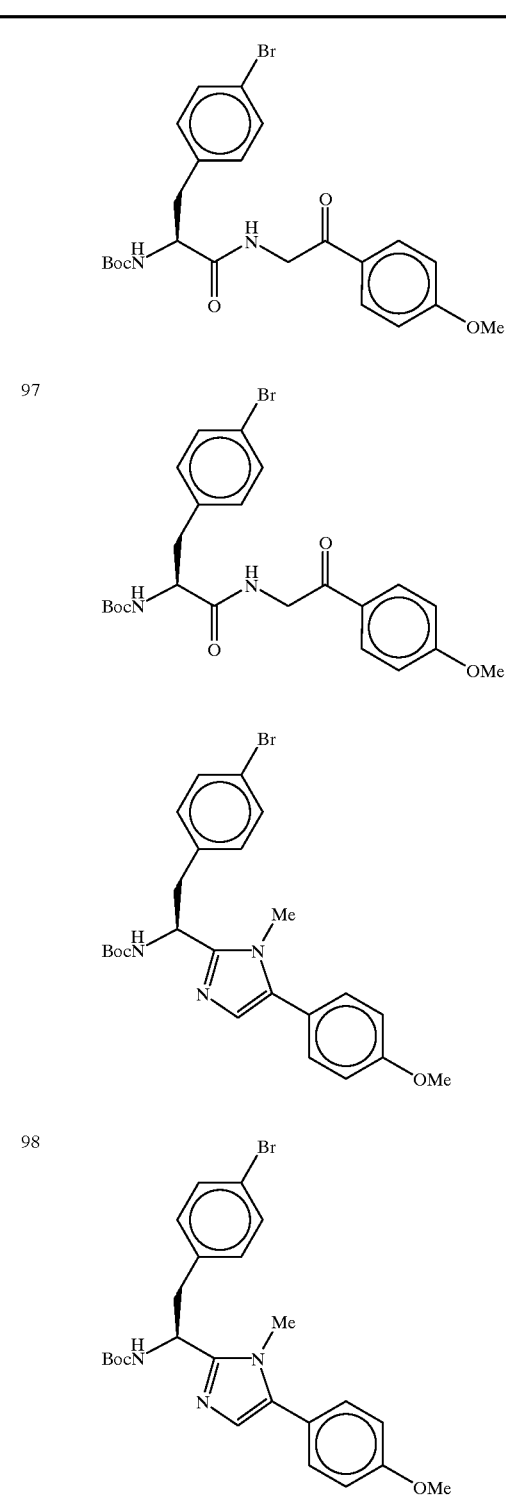 |
| 98 | |
TABLE-continued
| Preparation No. | Formula |
|---|---|
| 99 | 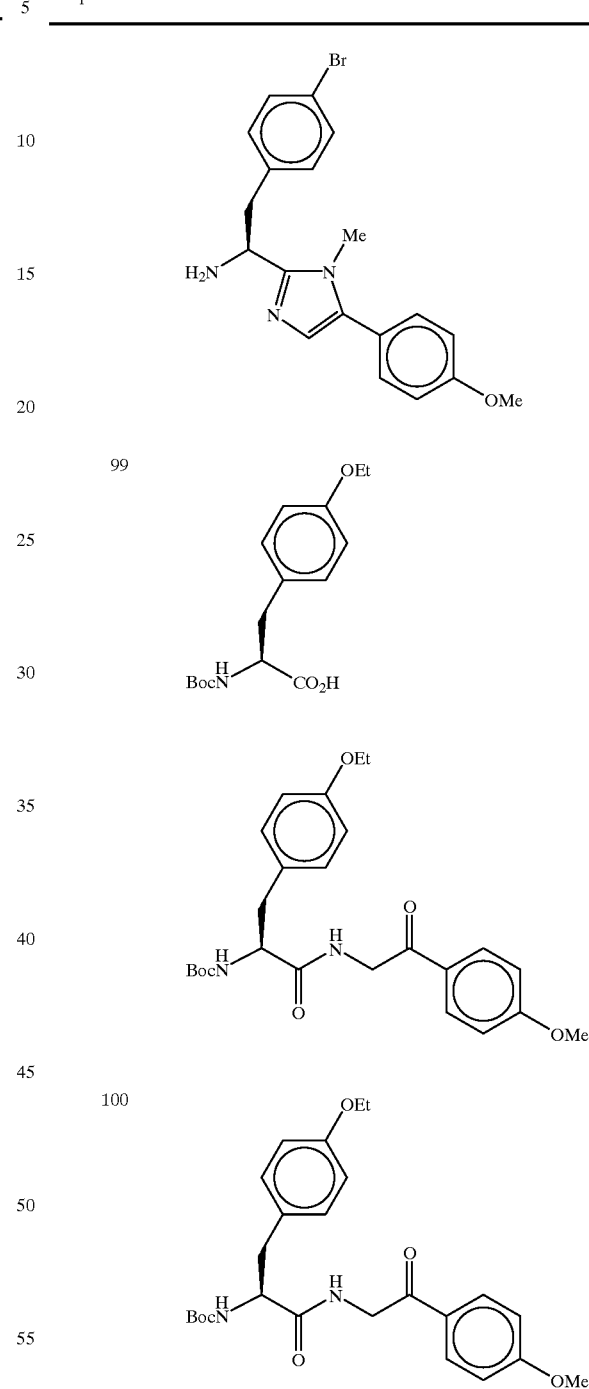 |
| 100 | |

TABLE-continued

| Preparation No. | Formula |
|---|---|
| 101 | (structure: BocNH-CH(CH₂-C₆H₄-OEt)-imidazole(N-Me)-C₆H₄-OMe) |
| 102 | (structure: H₂N-CH(CH₂-C₆H₄-OEt)-imidazole(N-Me)-C₆H₄-OMe) |
|  | (structure: BocNH-CH(CH₂-C₆H₄-OMe)-CO₂H) |

TABLE-continued

| Preparation No. | Formula |
|---|---|
|  | (structure: BocNH-CH(CH₂-C₆H₄-OMe)-C(O)NH-CH₂-C(O)-C₆H₄-OMe) |
| 103 | (structure: BocNH-CH(CH₂-C₆H₄-OMe)-C(O)NH-CH₂-C(O)-C₆H₄-OMe) |
|  | (structure: BocNH-CH(CH₂-C₆H₄-OMe)-imidazole(N-Me)-C₆H₄-OMe) |
| 104 | (structure: BocNH-CH(CH₂-C₆H₄-OMe)-imidazole(N-Me)-C₆H₄-OMe) |

TABLE-continued
| Preparation No. | Formula |
|---|---|
| 5 | 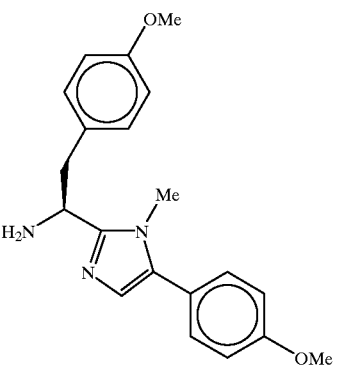 |
TABLE
| Example No. | Formula |
|---|---|
| 1 | 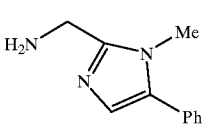 |
| 2 | 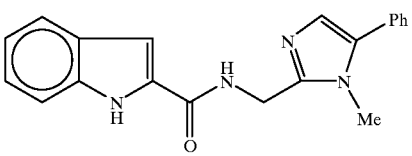 |
| 3 | 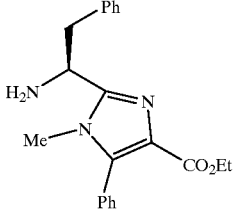 |
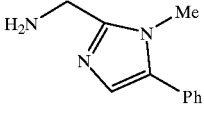

| Example No. | Formula |
|---|---|
| | (indole-2-carboxamide linked to N-methyl-5-phenyl-4-(ethoxycarbonyl)imidazol-2-yl with benzyl side chain) |
| 4 | (2-amino-3-phenylpropyl attached to 1-methyl-5-phenyl-4-(ethoxycarbonyl)imidazol-2-yl) |
| | (benzofuran-2-carboxamide linked to N-methyl-5-phenyl-4-(ethoxycarbonyl)imidazol-2-yl with benzyl side chain) |
| 5 | (2-amino-3-(4-methoxyphenyl)propyl attached to 1-methyl-5-phenylimidazol-2-yl) |
| | (indole-2-carboxamide linked to 1-methyl-5-phenylimidazol-2-yl with 4-methoxybenzyl side chain) |
| 6 | (2-amino-3-(4-methoxyphenyl)propyl attached to 1-methyl-5-phenylimidazol-2-yl) |

TABLE-continued
| Example No. | Formula |
|---|---|
|  | 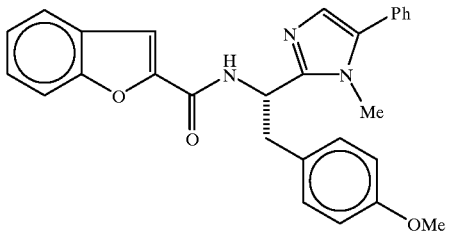 |
| 7 | 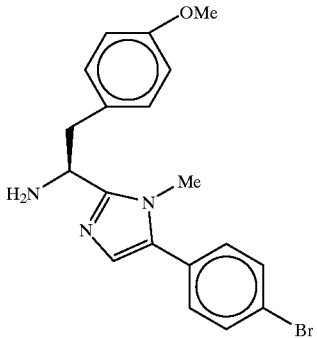 |
|  | 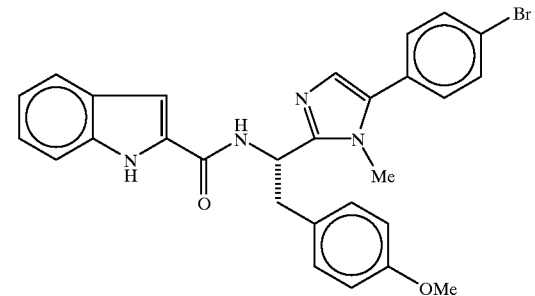 |
| 8 | 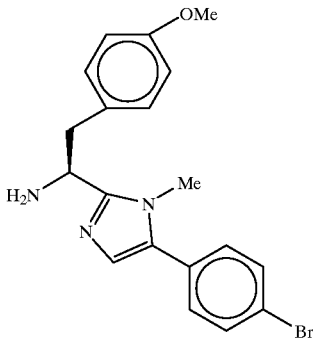 |
|  | 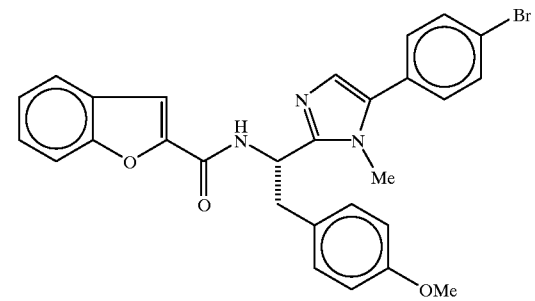 |

TABLE-continued

| Example No. | Formula |
|---|---|
| 9 | (structure: (S)-1-phenyl-3-[1-methyl-5-(4-methylthiophenyl)imidazol-2-yl]-3-aminopropane) |
|  | (structure: indole-2-carboxamide of the above amine, N-[(1S)-1-[1-methyl-5-(4-methylthiophenyl)imidazol-2-yl]-2-phenylethyl]-1H-indole-2-carboxamide) |
| 10 | (structure: (S)-1-phenyl-3-[1-methyl-5-(4-methylthiophenyl)imidazol-2-yl]-3-aminopropane, regioisomer) |
|  | (structure: benzofuran-2-carboxamide of the above amine) |
| 11 | (structure: (S)-1-(4-chlorophenyl)-2-[1-methyl-5-(4-bromophenyl)imidazol-2-yl]-2-aminoethane) |

TABLE-continued
| Example No. | Formula |
|---|---|
| | 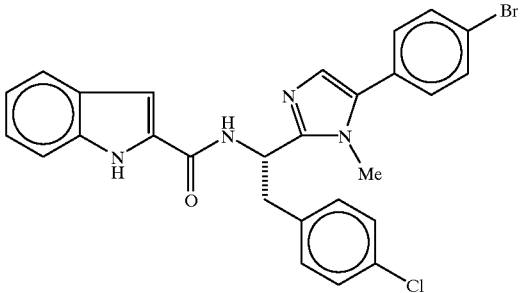 |
| 12 | 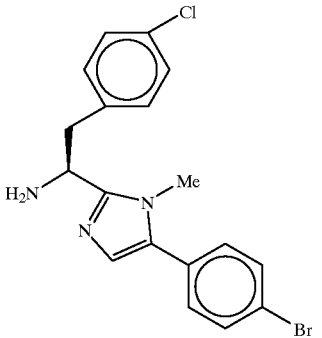 |
| | 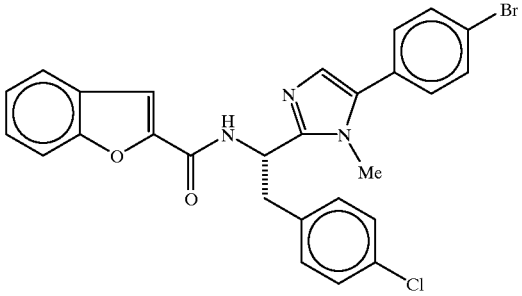 |
| 13 | 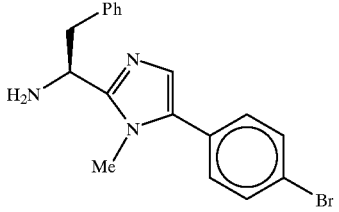 |
| | 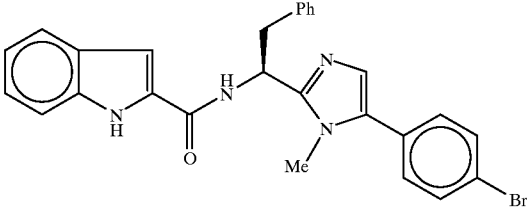 |

TABLE-continued

| Example No. | Formula |
|---|---|
| 14 | (structure: 2-(1-amino-2-phenylethyl)-5-(4-bromophenyl)-1-methylimidazole) |
| | (structure: benzofuran-2-carboxamide of the above amine) |
| 15 | (structure: 2-(1-amino-2-phenylethyl)-5-(4-chlorophenyl)-1-methylimidazole) |
| | (structure: indole-2-carboxamide of the above amine) |
| 16 | (structure: 2-(1-amino-2-phenylethyl)-5-(4-chlorophenyl)-1-methylimidazole) |
| | (structure: benzofuran-2-carboxamide of the above amine) |

TABLE-continued
| Example No. | Formula |
|---|---|
| 17 | 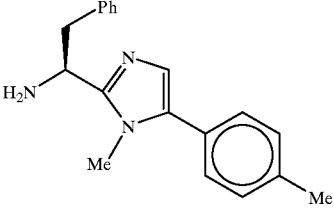 |
| 18 | 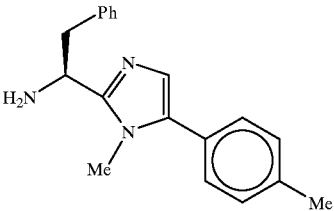 |
| 19 | 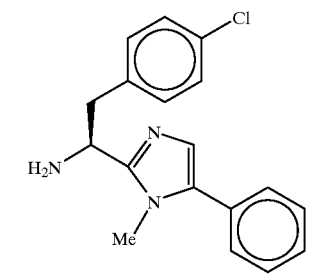 |

TABLE-continued

| Example No. | Formula |
| --- | --- |
| 20 | (structure: 1-(4-chlorophenyl)-2-(1-methyl-5-phenyl-1H-imidazol-2-yl)ethylamine) |
|  | (structure: N-[1-(4-chlorobenzyl)-2-(1-methyl-5-phenyl-1H-imidazol-2-yl)ethyl]benzofuran-2-carboxamide) |
| 21 | (structure: 1-[1-(4-methylbenzyl)-1H-imidazol-2-yl]-2-phenylethylamine) |
|  | (structure: N-{1-[1-(4-methylbenzyl)-1H-imidazol-2-yl]-2-phenylethyl}-1H-indole-2-carboxamide) |
| 22 | (structure: 1-(1-methyl-5-phenyl-1H-imidazol-2-yl)-2-phenylethylamine) |

TABLE-continued

| Example No. | Formula |
|---|---|
| 23 | |
| 24 | |
| 25 | |

TABLE-continued
| Example No. | Formula |
|---|---|
| 26 | 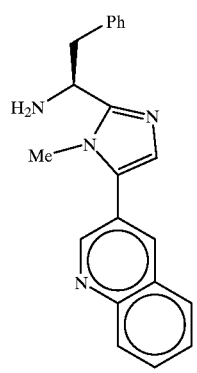<br>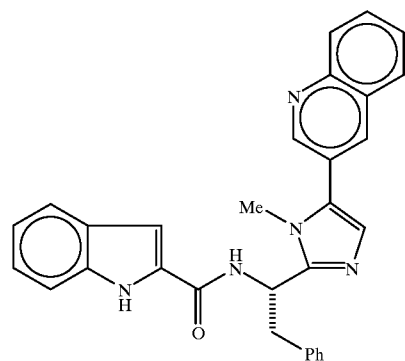 |
| 27 | 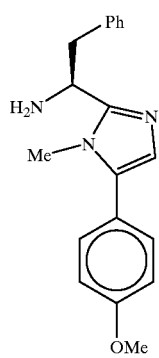<br>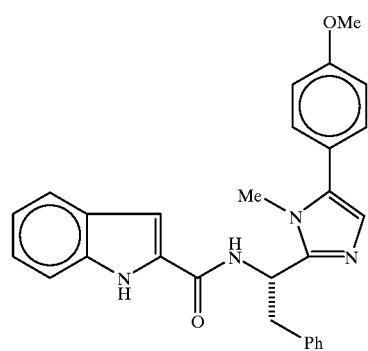 |

TABLE-continued
| Example No. | Formula |
| --- | --- |
| 28 | 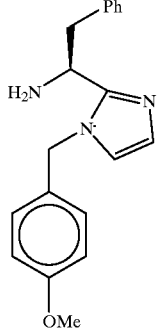 |
| 29 | 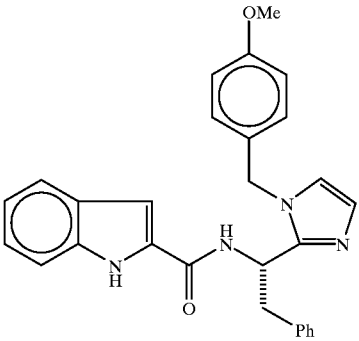 |
|  | 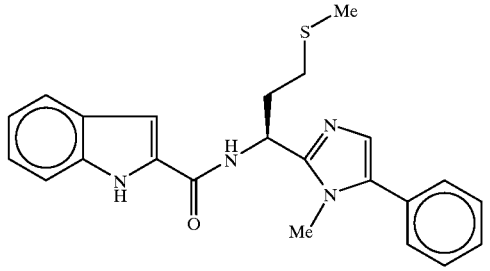 |

TABLE-continued
| Example No. | Formula |
|---|---|
| 30 | 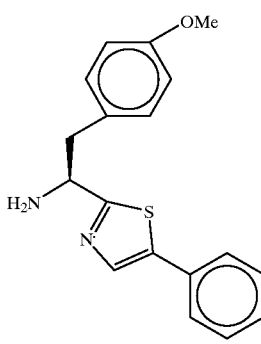 |
| 31 | 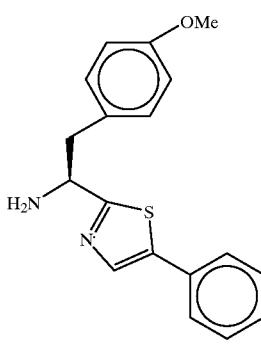 |
| 32 | 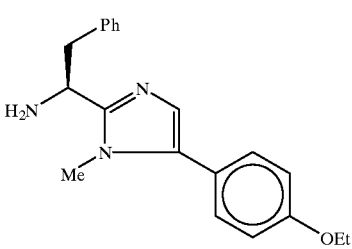 |

TABLE-continued
| Example No. | Formula |
|---|---|
|  | 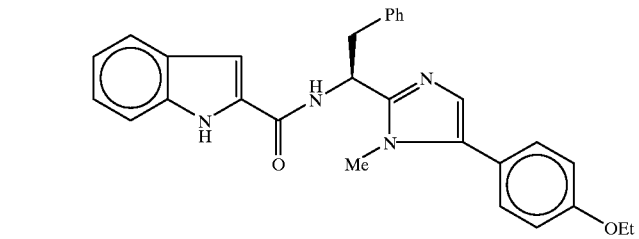 |
| 33 | 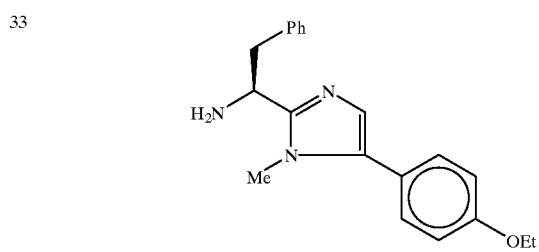 |
|  | 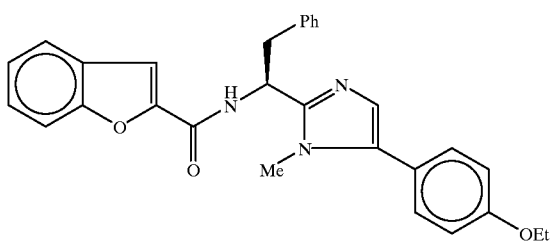 |
| 34 | 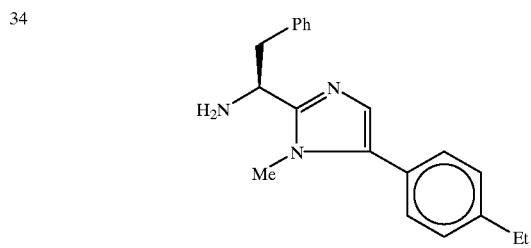 |
|  | 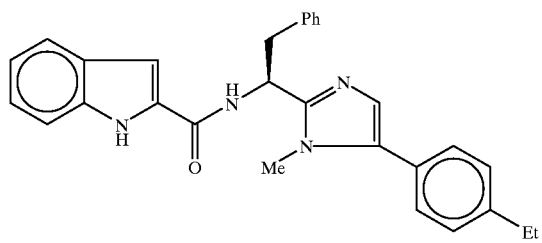 |
| 35 | 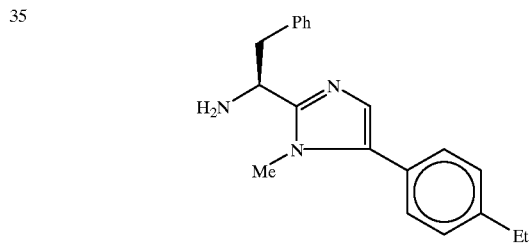 |

TABLE-continued

| Example No. | Formula |
| --- | --- |
|  | (benzofuran-2-carboxamide linked to (S)-1-phenyl-2-[1-methyl-5-(4-ethylphenyl)imidazol-2-yl]ethylamine) |
| 36 | (2-amino-1-(4-methoxybenzyl)-1-[1-methyl-5-(2-chlorophenyl)imidazol-2-yl] structure; and indole-2-carboxamide of the same amine) |
| 37 | (2-amino-1-(4-methoxybenzyl)-1-[1-methyl-5-(4-methylphenyl)imidazol-2-yl] structure; and indole-2-carboxamide of the same amine) |

TABLE-continued
| Example No. | Formula |
|---|---|
| 38 | 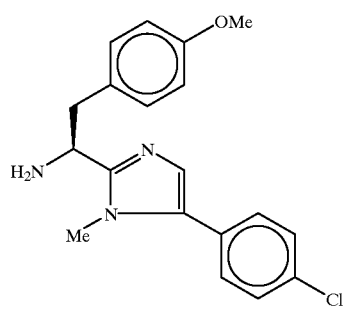 |
| 39 | 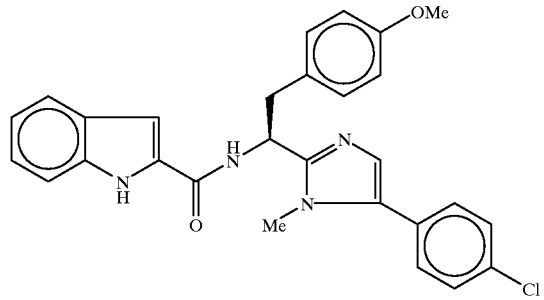 |
| 40 | 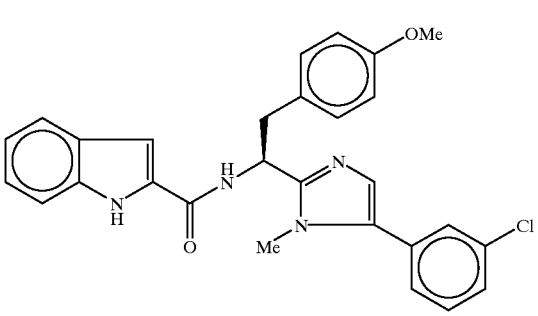 |

TABLE-continued

| Example No. | Formula |
|---|---|
| | (structure: indole-2-carboxamide linked to CH(CH2-C6H4-OMe)-imidazole(N-Me)-C6H4-F) |
| 41 | (structure: H2N-CH(CH2-C6H4-OMe)-imidazole(N-Me)-C6H4-OEt) |
| | (structure: indole-2-carboxamide linked to CH(CH2-C6H4-OMe)-imidazole(N-Me)-C6H4-OEt) |
| 42 | (structure: H2N-CH(CH2-C6H4-OMe)-imidazole(N-Me)-C6H4-Br) |
| | (structure: indole-3-carboxamide linked to CH(CH2-C6H4-OMe)-imidazole(N-Me)-C6H4-Br) |

TABLE-continued
| Example No. | Formula |
|---|---|
| 43 | 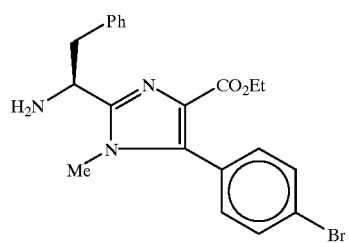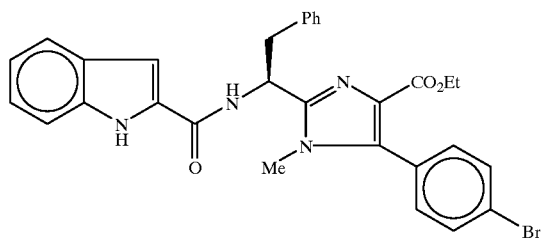 |
| 44 | 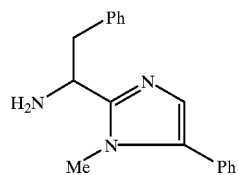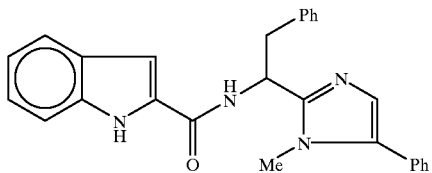 |
| 45 | 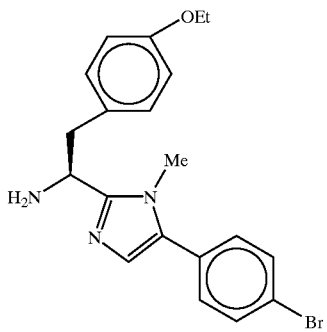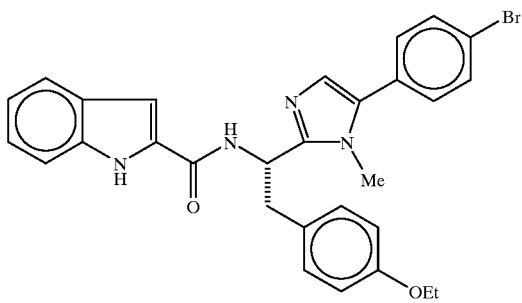 |

TABLE-continued
| Example No. | Formula |
| --- | --- |
| 46 | 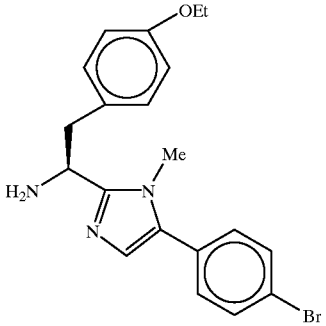 |
| 47 | 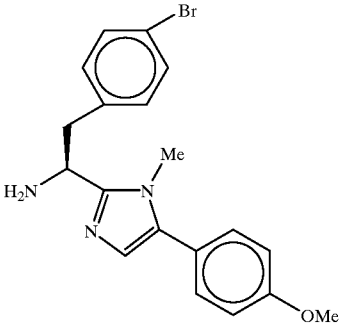 |
| | 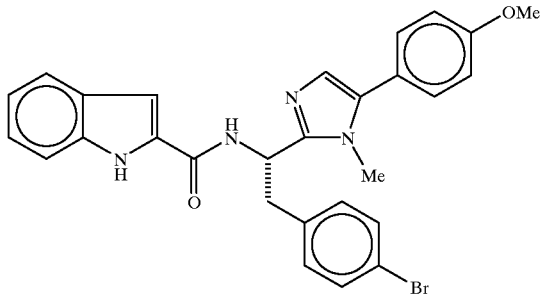 |

TABLE-continued
| Example No. | Formula |
|---|---|
| 48 | 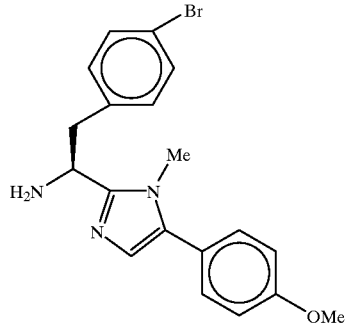 |
| 49 | 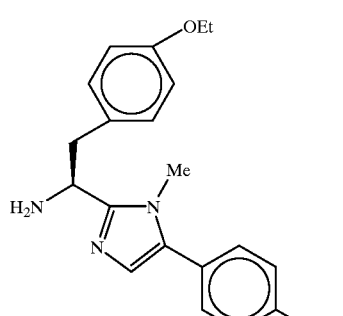 |
| | 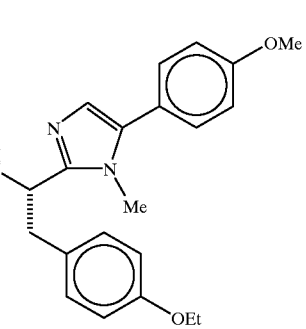 |

TABLE-continued

| Example No. | Formula |
|---|---|
| 50 | [structure: 1-methyl-2-(1-amino-2-(4-methoxyphenyl)ethyl)-5-(4-methoxyphenyl)imidazole] |
| | [structure: indole-2-carboxamide linked to 1-methyl-5-(4-methoxyphenyl)imidazol-2-yl with 4-methoxybenzyl substituent] |

Preparation 1

To an ice-cooled mixture of N-(tert-butoxycarbonyl) glycine (1.40 g) and 2-aminoacetophenone hydrochloride (1.61 g) in dichloromethane (14 ml) was added 1-(3-dimethylaminopropyl)-3-ethylcarbodiimide (1.49 g). The mixture was stirred at room temperature for 12 hours. A saturated aqueous sodium hydrogencarbonate solution was added to the mixture, and then the mixture was extracted three times with chloroform. The organic layer was washed with brine, dried over magnesium sulfate, filtered and concentrated. The residue was purified by column chromatography (silica gel, chloroform/methanol=40/1) to give the object compound as white powder (689 mg).

MASS (ESI) (m/z): 293 (M+H)$^+$ $^1$H-NMR (CDCl$_3$, 300 MHz) δ: 1.47(9H,s), 3.92(2H,d,J=5 Hz), 4.78(2H,s), 5.13(1H,br s), 7.05(1H,br s), 7.45–7.70(3H, m), 7.92–8.04(2H,m)

Preparation 2

A solution of the starting compound (669 mg) and 40% methylamine (0.7 ml) in a mixture of acetic acid (0.7 ml) and xylene (7 ml) was refluxed for 4 hours in a flask equipped with a Dean-Stark trap. The mixture was concentrated, neutralized with 1N hydroxide solution, and extracted three times with chloroform. The organic layer was washed with brine, dried over magnesium sulfate, filtered and concentrated. The residue was purified by column chromatography (silica gel, chloroform/methanol=50/1) to give the object compound as an oil (445 mg).

MASS (ESI) (m/z): 288 (M+H)$^+$ $^1$H-NMR (CDCl$_3$, 300 MHz) δ: 1.46(9H,s), 3.60(3H,s), 4.48(2H,d,J=5 Hz), 5.33(1H,br s), 6.99(1H,s), 7.30–7.52 (5H,m)

Preparation 3

The starting compound (430 mg) was dissolved in trifluoroacetic acid (1.5 ml) and the mixture was stirred at room temperature for 1 hour. The mixture was concentrated, made basic with 1N sodium hydroxide solution and extracted three times with chloroform. The organic layer was dried over magnesium sulfate and filtered. Evaporation of the solvent gave the object compound as an oil (314 mg).

MASS (ESI) (m/z): 188 (M+H)$^+$ $^1$H-NMR (CDCl$_3$, 300 MHz) δ: 3.57(3H,s), 3.98(2H,s), 6.98(1H,s), 7.26–7.50(5H,m)

Preparation 4

To a solution of the starting compound (2.12 g) in tetrahydrofuran (20 ml) was added successively isobutyl chloroformate (1.1 ml) and N-methylmorpholine (0.9 ml) at −25° C., and the mixture was stirred at the temperature for 5 minutes. The above mixture was added to a solution of dl-2-benzoylglycine ethyl ester hydrochloride (2.05 g) and N-methylmorpholine (0.9 ml) in tetrahydrofuran (5 ml) at −20° C., and the mixture was allowed to warm to room temperature for 2 hours. Water was added to the mixture, and the mixture was extracted three times with chloroform. The organic layer was washed with brine, dried over magnesium sulfate, filtered, and concentrated. The residue was purified by column chromatography (silica gel, hexane/ethyl acetate=3/1) to give the object compound as an oil (2.36 g).

MASS (ESI) (m/z): 455 (M+H)$^+$ $^1$H-NMR (CDCl$_3$, 300 MHz) δ: 1.13(3H,t,J=7 Hz), 1.41 (9H,s), 2.95–3.21(2H,m), 4.13(2H,q,J=7 Hz), 4.38–4.60 (1H,m), 4.83–5.05(1H,m), 6.02–6.20(1H,m), 7.10–7.37(6H, m), 7.42–7.71(3H,m), 8.01–8.18(2H,m)

Preparation 5

The object compound was obtained according to a similar manner to that of Preparation 2.

MASS (ESI) (m/z): 450 (M+H)$^+$ $^1$H-NMR (CDCl$_3$, 300 MHz) δ: 1.12(3H,t,J=7 Hz), 1.40 (9H,s), 2.68(3H,s), 3.08–3.42(2H,m), 4.21(2H,q,J=7 Hz), 4.89–5.05(1H,m), 5.77(1H,br d,J=8 Hz), 6.96–7.48(10H,m)

Preparation 6

The object compound was obtained according to a similar manner to that of Preparation 3.

MASS (ESI) (m/z): 350 (M+H)$^+$
$^1$H-NMR (CDCl$_3$,300 MHz) δ: 1.08(3H,t,J=7 Hz), 2.80 (3H,s), 3.21–3.48(2H,m), 4.15(2H,q,J=7 Hz), 4.25–4.72 (3H,m), 7.00–7.48(10H,m)

Preparation 7

The object compound was obtained according to a similar manner to that of Preparation 1.

MASS (ESI) (m/z): 413 (M+H)$^+$
$^1$H-NMR (CDCl$_3$,300 MHz) δ: 1.41(9H,s), 3.05(2H,d,J=6 Hz), 3.75(3H,s), 4.43(1H,br s), 4.58–4.81(2H,m), 5.05(1H, br s), 6.81(2H,d,J=8 Hz), 6.91(1H,br s), 7.12(2H,d,J=8 Hz), 7.42–7.68(3H,m), 7.95(2H,d,J=7 Hz)

Preparation 8

The object compound was obtained according to a similar manner to that of Preparation 2.

MASS (ESI) (m/z): 408 (M+H)$^+$
$^1$H-NMR (CDCl$_3$,300 MHz) δ: 1.42(9H,s), 3.00–3.33 (2H,m), 3.02(3H,s), 3.77(3H,s), 4.89–5.04(1H,m), 5.63(1H, d,J=8 Hz), 6.76(2H,d,J=8 Hz), 6.94(2H,d,J=8 Hz), 7.02(1H, s), 7.18–7.45(5H,m)

Preparation 9

To a solution of the starting compound (3.10 g) in methanol (15 ml) was added concentrated hydrochloric acid (3 ml), and the mixture was heated to 50° C. for 2 hours. The mixture was concentrated, made basic with a 1N sodium hydroxide solution, and extracted three times with chloroform. The organic layer was dried over magnesium sulfate, and filtered. Evaporation of the solvent gave the object compound (2.35 g).

MASS (ESI) (m/z): 308 (M+H)$^+$
$^1$H-NMR (CDCl$_3$,300 MHz) δ: 3.02–3.22(2H,m), 3.21 (3H,s), 3.78(3H,s), 4.11(1H,t,J=7 Hz), 6.81(2H,d,J=8 Hz), 6.99(2H,d,J=8 Hz), 7.04(1H,s), 7.21–7.48(5H,m)

Preparation 10

The object compound was obtained according to a similar manner to that of Preparation 1.

MASS (ESI) (m/z): 491,493 (M+H)$^+$
$^1$H-NMR (CDCl$_3$,300 MHz) δ: 1.41(9H,s), 3.04(2H,d,J=6 Hz), 3.75(3H,s), 4.42(1H,br s), 4.54–4.77(2H,m), 5.00(1H, br s), 6.81(2H,d,J=8 Hz), 6.85(1H,br s), 7.12(2H,d,J=8 Hz), 7.63(2H,d,J=7 Hz), 7.80(2H,d,J=7 Hz)

Preparation 11

The object compound was obtained according to a similar manner to that of Preparation 2.

MASS (ESI) (m/z): 486,488 (M+H)$^+$
$^1$H-NMR (CDCl$_3$,300 MHz)δ: 1.41(9H,s), 3.00(3H,s), 3.01–3.32(2H,m), 3.76(3H,s), 4.88–5.02(1H,m), 5.57(1H,d, J=8 Hz), 6.76(2H,d,J=8 Hz), 6.88–7.18(5H,m), 7.51(2H,d, J=8 Hz)

Preparation 12

The object compound was obtained according to a similar manner to that of Preparation 9.

MASS (ESI) (m/z): 386,388 (M+H)$^+$
$^1$H-NMR (CDCl$_3$,300 MHz) δ: 3.02–3.18(2H,m), 3.20 (3H,s), 3.78(3H,s), 4.12(1H,t,J=7 Hz), 6.81(2H,d,J=8 Hz), 6.98(2H,d,J=8 Hz), 7.03(1H,s), 7.15(2H,d,J=8 Hz), 7.52 (2H,d,J=8 Hz)

Preparation 13

The object compound was obtained according to a similar manner to that of Preparation 1.

MASS (ESI) (m/z): 429 (M+H)$^+$
$^1$H-NMR (CDCl$_3$,300 MHz) δ: 1.41(9H,s), 2.52(3H,s), 2.99–3.21(2H,m), 4.48(1H,br s), 4.53–4.79(2H,m), 5.03 (1H,br s), 6.90(1H,br s), 7.13–7.25(7H,m), 7.83(2H,d,J=8 Hz)

Preparation 14

The object compound was obtained according to a similar manner to that of Preparation 2.

MASS (ESI) (m/z): 424 (M+H)$^+$
$^1$H-NMR (CDCl$_3$,300 MHz) δ: 1.40(9H,s), 2.50(3H,s), 2.94(3H,s), 3.00–3.40(2H,m), 4.90–5.10(1H,m), 5.59(1H,br d,J=8 Hz), 6.95–7.35(10H,m)

Preparation 15

The object compound was obtained according to a similar manner to that of Preparation 9.

MASS (ESI) (m/z): 324 (M+H)$^+$
$^1$H-NMR (CDCl$_3$,300 MHz) δ: 2.50(3H,s), 3.08–3.27 (2H,m), 3.17(3H,s), 4.16(1H,t,J=7 Hz), 7.03(1H,s), 7.05–7.35(9H,m)

Preparation 16

The object compound was obtained according to a similar manner to that of Preparation 1.

MASS (ESI) (m/z): 495, 497 (M+H)$^+$
$^1$H-NMR (CDCl$_3$,300 MHz) δ: 1.40(9H,s), 2.98–3.20 (2H,m), 4.47(1H,m), 4.55–4.78(2H,m), 5.10(1H,br d,J=8 Hz), 7.01(1H,br s), 7.14(2H,d,J=8 Hz), 7.25(2H,d,J=8 Hz), 7.64(2H,d,J=8 Hz), 7.81(2H,d,J=8 Hz)

Preparation 17

The object compound was obtained according to a similar manner to that of Preparation 2.

MASS (ESI) (m/z): 490, 492 (M+H)$^+$
$^1$H-NMR (CDCl$_3$,300 MHz) δ: 1.39(9H,s), 3.12(3H,s), 3.13–3.22(2H,m), 4.91–5.08(1H,m), 5.47(1H,br d,J=9 Hz), 6.90–7.30(7H,m), 7.52(2H,d,J=8 Hz)

Preparation 18

The object compound was obtained according to a similar manner to that of Preparation 9.

MASS (ESI) (m/z): 390, 392 (M+H)$^+$
$^1$H-NMR (CDCl$_3$,300 MHz) δ: 3.02–3.26(2H,m), 3.27 (3H,s), 4.11(1H,t,J=7 Hz), 7.02(2H,d,J=8 Hz), 7.03(1H,s), 7.15(2H,d,J=8 Hz), 7.22(2H,d,J=8 Hz), 7.53(2H,d,J=8 Hz)

Preparation 19

The object compound was obtained according to a similar manner to that of Preparation 1.

amorphous solid

MASS: 461 (M+1)
$^1$H-NMR (CDCl$_3$) δ: 1.39(9H,s), 3.00–3.20(2H,m), 4.40–4.78(3H,m), 5.03(1H,bs), 6.89(1H,bs), 7.19–7.38(5H, m), 7.63(2H,d,J=8 Hz), 7.82(2H,d,J=8 Hz)

Preparation 20

The object compound was obtained according to a similar manner to that of Preparation 2.

mp: 162–164° C.

MASS: 456 (M+1)
$^1$H-NMR (CDCl$_3$) δ: 1.41(9H,s), 2.97(3H,s), 3.11(1×1/3H,d,J=8 Hz), 3.15(1×2/3H,d,J=8 Hz), 3.31(1×2/3H,d,J=8 Hz), 3.35(1×1/3H,d,J=8 Hz), 4.91–5.08(1H,m), 5.59(1H,d, J=8 Hz), 6.99–7.07(3H,m), 7.09(2H,d,J=8 Hz), 7.18–7.23 (3H,m), 7.51(2H,d,J=8 Hz)

Preparation 21

The object compound was obtained according to a similar manner to that of Preparation 3.

oil

MASS: 356 (M+1)
$^1$H-NMR (CDCl$_3$) δ: 3.10–3.25(2H,m), 3.20(3H,s), 4.17 (1H,t,J=8 Hz), 7.05(1H,s), 7.10(2H,d,J=8 Hz), 7.14(2H,d, J=8 Hz), 7.20–7.32(3H,m), 7.53(2H,d,J=8 Hz)

Preparation 22

The object compound was obtained according to a similar manner to that of Preparation 1.

amorphous solid

MASS: 417 (M+1)
$^1$H-NMR (CDCl$_3$) δ: 1.40(9H,s), 3.11(2H,d,J=8 Hz), 4.40–4.60(1H,m), 4.60–4.78(2H,m), 5.00(1H,bs), 6.84(1H, bs), 7.17–7.36(5H,m), 7.49(2H,d,J=8 Hz), 7.90(2H,d,J=8 Hz)

Preparation 23

The object compound was obtained according to a similar manner to that of Preparation 2.

amorphous solid

MASS: 412 (M+1)

$^1$H-NMR (CDCl$_3$) δ: 1.41(9H,s), 2.92(3H,s), 3.00–3.20 (1H,m), 3.24–3.40(1H,m), 5.00(1H,q,J=8 Hz), 5.59(1H,d, J=8 Hz), 7.00–7.10(3H,m), 7.14(2H,d,J=8 Hz), 7.18–7.30 (3H,m), 7.37(2H,d,J=8 Hz)

Preparation 24

The object compound was obtained according to a similar manner to that of Preparation 3.

oil

MASS: 312 (M+1)

$^1$H-NMR (CDCl$_3$) δ: 3.10–3.28(2H,m), 3.18(3H,s), 4.10–4.24(1H,m), 7.08(2H,d,J=8 Hz), 7.11(1H,s), 7.21(2H, d,J=8 Hz), 7.22–7.33(3H,m), 7.39(2H,d,J=8 Hz)

Preparation 25

The object compound was obtained according to a similar manner to that of Preparation 1.

mp: 135–139° C.

MASS: 397 (M+1)

$^1$H-NMR (CDCl$_3$) δ: 1.41(9H,s), 2.41(3H,s), 3.00–3.20 (2H,m), 4.50(1H,d,J=5 Hz), 4.57–4.78(2H,m), 5.07(1H,d, J=5 Hz), 6.91(1H,s), 7.18–7.33(7H,m), 7.83(2H,d,J=8 Hz)

Preparation 26

The object compound was obtained according to a similar manner to that of Preparation 2.

mp: 131–133° C.

MASS: 392 (M+1)

$^1$H-NMR (CDCl$_3$) δ: 1.39(9H,s), 2.38(3H,s), 2.97(3H,s), 3.11(1×1/3H,d,J=8 Hz), 3.17(1×2/3H,d,J=8 Hz), 3.31(1×2/3H,d,J=8 Hz), 3.36(1×1/3H,d,J=8 Hz), 4.93–5.08(1H,m), 5.59(1H,d,J=8 Hz), 7.00(1H,s), 7.01–7.09(2H,m), 7.09–7.16 (2H,m), 7.16–7.28(5H,m)

Preparation 27

The object compound was obtained according to a similar manner to that of Preparation 3.

oil

MASS: 292 (M+1)

$^1$H-NMR (CDCl$_3$) δ: 2.37(3H,s), 3.10–3.27(2H,m), 3.19 (3H,s), 4.17(1H,t,J=8 Hz), 7.01(1H,s), 7.09(2H,d,J=8 Hz), 7.12–7.33(7H,m)

Preparation 28

To an ice-cooled mixture of the starting compound (599 mg), 2-aminoacetophenone hydrochloride (362 mg) and 1-hydroxybenzotriazole (270 mg) in dichloromethane (6 ml) was added 1-(3-dimethylaminopropyl)-3-ethylcarbodiimide (349 mg). The mixture was stirred at room temperature for 12 hours. A saturated aqueous sodium hydrogencarbonate solution was added to the mixture, and then the mixture was extracted three times with chloroform. The organic layer was washed with brine, dried over magnesium sulfate, filtered, and concentrated. The residue was purified by column chromatography (silica gel, chloroform/methanol= 70/1) to give the object compound (823 mg).

MASS (ESI) (m/z): 417 (M+H)$^+$ $^1$H-NMR (CDCl$_3$,300 MHz) δ: 1.41(9H,s), 2.96–3.20 (2H,m), 4.47(1H,m), 4.70(2H,AB of ABX,J$_{A\ B}$=15 Hz), 5.01(1H,br s), 6.92(1H,br s), 7.13(2H,d,J=8 Hz), 7.24(2H, d,J=8 Hz), 7.41–7.68(3H,m), 7.88–8.00(2H,m)

Preparation 29

The object compound was obtained according to a similar manner to that of Preparation 2.

MASS (ESI) (m/z): 412 (M+H)$^+$ $^1$H-NMR (CDCl$_3$,300 MHz) δ: 1.40(9H,s), 3.13(3H,s), 3.15–3.32(2H,m), 4.92–5.07(1H,m), 5.58(1H,br d,J=8 Hz), 6.93–7.55(10H,m)

Preparation 30

The object compound was obtained according to a similar manner to that of Preparation 3.

MASS (ESI) (m/z): 312 (M+H)$^+$ $^1$H-NMR (CDCl$_3$,300 MHz) δ: 3.06–3.25(2H,m), 3.24 (3H,s), 4.17(1H,t,J=7 Hz), 6.98–7.50(10H,m)

Preparation 31

The starting compound (1.1 g) and glyoxal trimeric dihydrate (930 mg) were stirred in methanol (7 ml) at −10° C. Ammonia was bubbled through the solution for 5 minutes and the mixture was stirred at −10° C. for 1 hour. The mixture was allowed to warm to room temperature over 18 hours, then poured into water, and extracted twice with dichloromethane. The combined extracts was dried over anhydrous magnesium sulfate and concentrated in vacuo. The residue was purified by flash column chromatography over silica gel with a dichloromethane-methanol gradient (20:1 and 10:1) as eluent to give the object compound as an off-white solid (698.6 mg).

mp: 180.5–184° C.

MASS: 288 (M+H)$^+$ $^1$H-NMR (CDCl$_3$) δ: 1.40(9H,s), 3.29(2H,d,J=7.5 Hz), 4.90(1H,q,J=7.5 Hz), 5.25(1H,bd,J=7.5 Hz), 6.89(1H,bs), 6.99(1H,bs), 7.12(2H,d,J=7.5 Hz), 7.18–7.30(3H,m), 9.78 (1H,bs)

Preparation 32

To a precooled solution of the starting compound (500 mg) in N,N-dimethylformamide (5 ml) was added 85% potassium hydroxide powder (115 mg). After the mixture was stirred for 1 hour on an ice bath, α-chloro-p-xylene (230.4 μl) was added dropwise to the reaction mixture. The resulting suspension was stirred at 5° C. for 14 hours, then poured into water, and extracted with chloroform. The organic layer was washed twice with water and a saturated sodium chloride solution, dried over anhydrous magnesium sulfate, and concentrated in vacuo. The residue was washed with diethyl ether to give the object compound as a colorless solid (418.3 mg).

mp: 157–158.5° C.

MASS: 392 (M+H)$^+$ $^1$H-NMR (CDCl$_3$) δ: 1.36(9H,s), 2.30(3H,s), 3.19(2H,m), 4.63(1H,d,J=16.0 Hz), 4.71(1H,d,J=16.0 Hz), 5.01(1H,m), 5.32(1H,m), 6.63(1H,s), 6.77(2H,d,J=7.5 Hz), 6.98–7.23 (8H,m)

Preparation 33

The object compound was obtained according to a similar manner to that of Preparation 3.

colorless oil

MASS: 292 (M+H)$^+$ $^1$H-NMR (CDCl$_3$) δ: 2.31(3H,s), 3.02(1H,dd,J=13.5 and 7.5 Hz), 3.12(1H,dd,J=13.5 and 7.5 Hz), 4.06(1H,t,J=7.5 Hz), 4.76(1H,d,J=14.5 Hz), 4.83(1H,d,J=14.5 Hz), 6.71(1H, s), 6.86(2H,d,J=7.5 Hz), 6.99–7.04(3H,m), 7.10(2H,d,J=7.5 Hz), 7.20–7.30(3H,m)

Preparation 34

The object compound was obtained according to a similar manner to that of Preparation 1.

white crystals mp: 134–135° C.

MASS (ESI) (m/z): 383 (M+H)$^+$ $^1$H-NMR (CDCl$_3$,300 MHz) δ: 1.41(9H,s), 3.00–3.22 (2H,m), 4.47(1H,m), 4.69(2H,AB of ABX, J$_{A\ B}$=19 Hz), 5.03(1H,br s), 6.90(1H,br s), 7.16–7.68(8H,m), 7.95(2H,d, J=8 Hz)

Preparation 35

The object compound was obtained according to a similar manner to that of Preparation 2.

white crystals
mp: 130–131° C.
MASS (ESI) (m/z): 378 (M+H)+
$^1$H-NMR (CDCl$_3$,300 MHz) δ: 1.41(9H,s), 2.96(3H,s), 3.06–3.20(1H,m), 3.28–3.40(1H,m), 4.92–5.06(1H,m), 5.57 (1H,br d,J=9 Hz), 7.00–7.43(11H,m)

Preparation 36

The object compound was obtained according to a similar manner to that of Preparation 3.
white powder
MASS (ESI) (m/z): 278 (M+H)+
$^1$H-NMR (CDCl$_3$,300 MHz) δ: 3.10–3.28(2H,m), 3.18 (3H,s), 4.16(1H,t,J=7 Hz), 7.05(1H,s), 7.07–7.45(10H,m)

Preparation 37

The starting compound (600 mg) was heated at 40° C. for 2 hours in methyl iodide (10 ml). The reaction mixture was evaporated, and the residue was suspended in an aqueous sodium carbonate solution. The mixture was extracted with chloroform. The organic layer was washed successively with water and a saturated sodium chloride solution, dried over anhydrous magnesium sulfate and concentrated in vacuo. The residue was purified by flash column chromatography over silica gel with a chloroform-methanol (20:1) as eluent to give the object compound as a pale yellow oily solid (376.5 mg).
mp: 116–119° C.
MASS (ESI) (m/z): 302 (M+H)+
$^1$H-NMR (CDCl$_3$, δ) 1.40(9H,s), 3.05(3H,s), 3.10(1H,dd, J=14.5, 9.0 Hz), 3.29(1H,dd,J=14.5, 4.5 Hz), 4.93(1H,m), 5.50(1H,br d,J=7.5 Hz), 6.63(1H,s), 6.95–7.02(3H,m), 7.15–7.24(3H,m)

Preparation 38

The object compound was obtained according to a similar manner to that of Preparation 3.
yellow oil
MASS (ESI) (m/z): 202 (M+H)+
$^1$H-NMR (CDCl$_3$, δ) 3.09(1H,dd,J=14.5, 7.5 Hz), 3.13 (1H,dd,J=14.5, 7.5 Hz), 3.23(3H,s), 4.12(1H,t,J=7.5 Hz), 6.69(1H,s), 6.99(1H,s), 7.03(2H,d,J=7.5 Hz), 7.16–7.32(3H, m)

Preparation 39

The object compound was obtained according to a similar manner to that of Preparation 3.
yellow oil
MASS (ESI) (m/z): 188 (M+H)+
$^1$H-NMR (CDCl$_3$, δ) 2.82(1H,dd,J=14.5, 8.5 Hz), 3.37 (1H,dd,J=14.5, 2.5 Hz), 4.35(1H,dd,J=8.5, 2.5 Hz), 6.99(2H, s), 7.12(2H,d,J=7.5 Hz), 7.20–7.34(4H,m)

Preparation 40

A mixture of 6-acetylquinoline (2.0 g), hydroxylamine hydrochloride (1.0 g) and sodium carbonate (1.7 g) in ethanol (20 ml) was refluxed for 1 hour. After cooling to room temperature, water was added to the mixture. The precipitate was collected and washed with diethyl ether to give the object compound as a pale yellow solid (1.7 g).
mp: 170–173° C.
MASS (ESI) (m/z): 187 (M+H)+
$^1$H-NMR (CDCl$_3$, δ) 2.43(3H,s), 7.44(1H,dd,J=7.5, 4.5 Hz), 8.00(1H,s), 8.16–8.23(3H,m), 8.94(1H,d,J=4.5 Hz), 9.46(1H,s)

Preparation 41

To a solution of the starting compound (1.50 g) in pyridine (15 ml) cooled to 0° C. was added p-toluenesulfonyl chloride (1.84 g) with stirring under an atmosphere of nitrogen, and the mixture was stirred at 0° C. for 9 hours. After the reaction mixture was poured into ice-water, the precipitate was collected and washed successively with water and 2-propanol to give the object compound as a pale brown solid (1.62 g).
mp: 119.5–121° C.
MASS (ESI) (m/z): 341 (M+H)+
$^1$H-NMR (CDCl$_3$, δ) 2.43(3H,s), 2.48(3H,s), 7.36(2H,d, J=7.5 Hz), 7.44(1H,dd,J=7.5, 4.5 Hz), 7.92–8.03(4H,m), 8.07(1H,d,J=7.5 Hz), 8.18(1H,d,J=7.5 Hz), 8.95(1H,d,J=4.5 Hz)

Preparation 42

Potassium (258.4 mg) was added to a suspension of the starting compound (1.5 g) in ethanol (40 ml), and the mixture was stirred at room temperature for 72 hours. The precipitate of potassium p-toluenesulfonate was removed by filtration, and the filtrate was diluted with diethyl ether (400 ml). A further precipitate of the potassium salt was filtered off, and the ethereal solution was extracted twice with 1.5N hydrochloric acid (50 ml). The combined extracts were evaporated in vacuo, and the residue was recrystallized from 2-propanol to give the object compound as an off-white solid (1.31 g).
mp: 293.5–296° C.
MASS (ESI) (m/z): 187 (M+H)+
$^1$H-NMR (DMSO-d$_6$, δ) 4.72(1H,d,J=5.5 Hz), 4.77(1H, d,J=5.5 Hz), 7.83(1H,dd,J=7.5, 5.5 Hz), 8.30(1H,d,J=7.5 Hz), 8.37(1H,d,J=7.5 Hz), 8.55(2H,br s), 8.81(1H,d,J=7.5 Hz), 8.97(1H,s), 9.20(1H,d,J=5.5 Hz)

Preparation 43

The object compound was obtained according to a similar manner to that of Preparation 28.
pale yellow solid
MASS (ESI) (m/z): 434 (M+H)+
$^1$H-NMR (CDCl$_3$, δ) 1.42(9H,s), 3.15(2H,d,J=7.5 Hz), 4.50(1H,m), 4.80(1H,dd,J=20.5, 5.5 Hz), 4.89(1H,dd,J= 20.5, 5.5 Hz), 5.03(1H,m), 6.95(1H,m), 7.19–7.35(5H,m), 7.52(1H,dd,J=7.5, 5.5 Hz), 8.16–8.27(2H,m), 8.30(1H,d,J= 7.5 Hz), 8.48(1H,s), 9.07(1H,d,J=5.5 Hz)

Preparation 44

The object compound was obtained according to a similar manner to that of Preparation 2.
pale violet amorphous solid
MASS (ESI) (m/z): 429 (M+H)+
$^1$H-NMR (CDCl$_3$, δ) 1.42(9H,s), 3.05(3H,s), 3.18(1H,dd, J=13.5, 8.5 Hz), 3.37(1H,dd,J=13.5, 6.0 Hz), 5.03(1H,m), 5.59(1H,br d,J=7.5 Hz), 7.03–7.11(2H,m), 7.18(1H,s), 7.20–7.31(3H,m), 7.44(1H,dd,J=7.5, 5.5 Hz), 7.57(1H,d,J= 7.5 Hz), 7.70(1H,s), 8.15(2H,t,J=7.5 Hz), 8.95(1H,d,J=5.5 Hz)

Preparation 45

The object compound was obtained according to a similar manner to that of Preparation 3.
pale yellow oil
MASS (ESI) (m/z): 329 (M+H)+
$^1$H-NMR (CDCl$_3$, δ) 3.13–3.30(2H,m), 3.27(3H,s), 4.20 (1H,t,J=7.5 Hz), 7.08–7.15(2H,m), 7.18(1H,s), 7.21–7.34 (3H,m) 7.43(1H,dd,J=7.5, 5.5 Hz) 7.63(1H,d,J=7.5 Hz), 7.73(1H,s), 8.15(2H,t,J=7.5 Hz), 8.93(1H,d,J=5.5 Hz)

Preparation 46

The object compound was obtained according to a similar manner to that of Preparation 40.
off-white solid
mp: 205–208° C.
MASS (ESI) (m/z): 187 (M+H)+
$^1$H-NMR (CDCl$_3$–CD$_3$OD, δ) 2.40(3H,s), 7.59(1H,t,J= 7.5 Hz), 7.73(1H,t,J=7.5 Hz), 7.87(1H,d,J=7.5 Hz), 8.10 (1H,d,J=7.5 Hz), 8.28(1H,d,J=1.0 Hz), 9.46(1H,d,J=1.0 Hz)

Preparation 47

The object compound was obtained according to a similar manner to that of Preparation 41.

pale brown solid
mp: 165–174° C.
MASS (ESI) (m/z): 341 (M+H)$^+$
$^1$H-NMR (CDCl$_3$, δ) 2.44(3H,s), 2.47(3H,s), 7.39(1H,d, J=7.5 Hz), 7.60(1H,t,J=7.5 Hz), 7.79(1H,t,J=7.5 Hz), 7.85 (1H,d,J=7.5 Hz), 7.98(2H,d,J=7.5 Hz), 8.11(1H,d,J=7.5 Hz), 8.28(1H,d,J=1.5 Hz), 9.14(1H,d,J=1.5 Hz)

Preparation 48

The object compound was obtained according to a similar manner to that of Preparation 42.
off-white solid
mp: 290–294° C.
MASS (ESI) (m/z): 187 (M+H)$^+$
$^1$H-NMR (DMSO-d$_6$, δ) 4.75(1H,d,J=5.5 Hz), 4.79(1H, d,J=5.5 Hz), 7.80(1H,t,J=7.5 Hz), 8.02(1H,t,J=7.5 Hz), 8.18 (1H,d,J=7.5 Hz), 8.25(1H,d,J=7.5 Hz), 8.61(2H,br s), 9.27 (1H,d,J=1.0 Hz), 9.41(1H,d,J=1.0 Hz)

Preparation 49

The object compound was obtained according to a similar manner to that of Preparation 28.
pale yellow amorphous solid
MASS (ESI) (m/z): 434 (M+H)$^+$
$^1$H-NMR (CDCl$_3$, δ) 1.43(9H,s), 3.10–3.19(2H,m), 4.51 (1H,m), 4.79(1H,dd,J=20.5, 4.5 Hz), 4.88(1H,dd,J=20.5, 4.5 Hz), 5.03(1H,m), 6.93(1H,m), 7.17–7.34(5H,m), 7.69(1H,t, J=7.5 Hz), 7.90(1H,t,J=7.5 Hz), 7.97(1H,d,J=7.5 Hz), 8.18 (1H,d,J=7.5 Hz), 8.73(1H,d,J=1.0 Hz), 9.40(1H,d,J=1.0 Hz)

Preparation 50

The object compound was obtained according to a similar manner to that of Preparation 2.
pale brown amorphous solid
MASS (ESI) (m/z): 429 (M+H)$^+$
$^1$H-NMR (CDCl$_3$, δ) 1.45(9H,s), 3.03(3H,s), 3.17(1H,dd, J=13.0, 9.0 Hz), 3.39(1H,dd,J=13.0, 5.5 Hz), 5.05(1H,m), 5.63(1H,d,J=7.5 Hz), 7.03–7.12(2H,m), 7.19–7.38(4H,m), 7.60(1H,t,J=7.5 Hz), 7.76(1H,t,J=7.5 Hz), 7.83(1H,d,J=7.5 Hz), 8.00(1H,d,J=1.0 Hz), 8.12(1H,d,J=7.5 Hz), 8.80(1H,d, J=1.0 Hz)

Preparation 51

The object compound was obtained according to a similar manner to that of Preparation 3.
pale brown amorphous solid
MASS (ESI) (m/z): 329 (M+H)$^+$
$^1$H-NMR (CDCl$_3$, δ) 3.18–3.25(2H,m), 3.22(3H,s), 4.21 (1H,t,J=7.5 Hz), 7.06–7.13(2H,m), 7.20–7.36(4H,m), 7.60 (1H,t,J=7.5 Hz), 7.76(1H,t,J=7.5 Hz), 7.83(1H,d,J=7.5 Hz), 8.04(1H,d,J=1.5 Hz), 8.12(1H,d,J=7.5 Hz), 8.83(1H,d,J=1.5 Hz)

Preparation 52

The object compound was obtained according to a similar manner to that of Preparation 1.
mp: 144–146° C.
MASS: 413 (M+1)
$^1$H-NMR (CDCl$_3$) δ: 1.41(9H,s), 3.00–3.20(2H,m), 3.87 (3H,s), 4.49(1H,d,J=5 Hz), 4.53–4.74(2H,m), 5.08(1H,d,J=5 Hz), 6.95(3H,d,J=8 Hz), 7.19–7.32(5H,m), 7.92(2H,d,J=8 Hz)

Preparation 53

The object compound was obtained according to a similar manner to that of Preparation 2.
mp: 125–128° C.
MASS: 408 (M+1)
$^1$H-NMR (CDCl$_3$) δ: 1.38(9H,s), 2.93(3H,s), 3.11(1×1/3H,d,J=8 Hz), 3.17(1×2/3H,d,J=8 Hz), 3.31(1×2/3H,d,J=6 Hz), 3.37(1×1/3H,d,J=6 Hz), 3.83(3H,s), 4.99(1H,q,J=8 Hz), 5.59(1H,d,J=8 Hz), 6.92(2H,d,J=8 Hz), 6.98(1H,s), 7.00–7.10(2H,m) 7.14(2H,d,J=8 Hz), 7.20–7.30(3H,m)

Preparation 54

The object compound was obtained according to a similar manner to that of Preparation 3.
oil
MASS: 308 (M+1)
$^1$H-NMR (CDCl$_3$) δ: 3.08–3.28(2H,m), 3.12(3H,s), 3.81 (3H,s), 4.17(1H,t,J=8 Hz), 6.94(2H,d,J=8 Hz), 6.99(1H,s), 7.09(2H,d,J=8 Hz), 7.11–7.40(5H,m)

Preparation 55

The object compound was obtained according to a similar manner to that of Preparation 32.
colorless solid
mp: 144–150° C.
MASS (ESI) (m/z): 408 (M+H)$^+$
$^1$H-NMR (CDCl$_3$, δ) 1.37(9H,s), 3.20(2H,m), 3.78(3H,s), 4.59(1H,d,J=14.5 Hz), 4.70(1H,d,J=14.5 Hz), 5.03(1H,m), 5.35(1H,m), 6.61(1H,s), 6.76(2H,d,J=9.0 Hz), 6.81(2H,d,J= 9.0 Hz), 6.97–7.06(3H,m), 7.17–7.23(3H,m)

Preparation 56

The object compound was obtained according to a similar manner to that of Preparation 3.
off-white oil
MASS (ESI) (m/z): 308 (M+H)$^+$
$^1$H-NMR (CDCl$_3$, δ) 3.03(1H,dd,J=14.5, 7.5 Hz), 3.14 (1H,dd,J=14.5, 7.5 Hz), 3.77(3H,s), 4.09(1H,t,J=7.5 Hz), 4.73(1H,d,J=15.0 Hz), 4.81(1H,d,J=15.0 Hz), 6.71(1H,s), 6.81(2H,d,J=7.5 Hz), 6.91(2H,d,J=7.5 Hz), 7.01–7.07(3H, s), 7.19–7.30(3H,m)

Preparation 57

The object compound was obtained according to a similar manner to that of Preparation 28.
pale yellow oil
MASS (ESI) (m/z): 367 (M+H)$^+$
$^1$H-NMR (CDCl$_3$, δ) 1.47(9H,s), 1.98(1H,m), 2.13(3H,s), 2.16(1H,m), 2.61(2H,t,J=7.5 Hz), 4.41(1H,m), 4.77(2H,t,J= 4.5 Hz), 5.23(1H,m), 7.14(1H,m), 7.50(2H,t,J=7.5 Hz), 7.63 (1H,t,J=7.5 Hz), 7.98(2H,d,J=7.5 Hz)

Preparation 58

The object compound was obtained according to a similar manner to that of Preparation 2.
pale brown oil
MASS (ESI) (m/z): 362 (M+H)$^+$
$^1$H-NMR (CDCl$_3$, δ) 1.43(9H,s), 2.12(3H,s), 2.12–2.61 (4H,m), 3.63(3H,s), 5.05–5.26(2H,m), 7.01(1H,s), 7.33–7.51(5H,m)

Preparation 59

The object compound was obtained according to a similar manner to that of Preparation 3.
pale yellow oil
MASS (ESI) (m/z): 262 (M+H)$^+$
$^1$H-NMR (CDCl$_3$, δ) 2.08(1H,m), 2.11(3H,s), 2.25(1H, m), 2.55–2.77(2H,m), 3.61(3H,s), 4.20(1H,t,J=7.5 Hz), 7.01 (1H,s), 7.33–7.48(5H,m)

Preparation 60

To a solution of the starting compound (893 mg) in tetrahydrofuran (4.5 ml) was added 2,4-bis(4-methoxyphenyl)-1,3-dithia-2,4-diphosphetane-2,4-disulfide (552 mg). The mixture was stirred at 50° C. for 4.5 hours, then allowed to cool to room temperature and concentrated. The crude product was purified by column chromatography (silica gel, chloroform) to give the object compound as pale orange powder (476 mg).
MASS (ESI) (m/z): 489, 491 (M+H)$^+$
$^1$H-NMR (CDCl$_3$, 300 MHz) δ: 1.41(9H,s), 3.12–3.32 (2H,m), 3.76(3H,s), 5.11–5.31(2H,m), 6.80(2H,d,J=8 Hz), 7.02(2H,d,J=8 Hz), 7.36(2H,d,J=8 Hz), 7.50(2H,d,J=8 Hz), 7.87(1H,s)

Preparation 61

The object compound was obtained according to a similar manner to that of Preparation 9.

MASS (ESI) (m/z): 389,391 (M+H)$^+$ $^1$H-NMR (CDCl$_3$,300 MHz) δ: 2.84(1H,dd,J=13 and 9 Hz), 3.31(1H,dd,J=13 and 5 Hz), 3.78(3H,s), 4.46(1H,dd, J=9 and 5 Hz), 6.86(2H,d,J=8 Hz), 7.13(2H,d,J=8 Hz), 7.40(2H,d,J=8 Hz), 7.51(2H,d,J=8 Hz), 7.88(1H,s)

Preparation 62

The object compound was obtained according to a similar manner to that of Preparation 28.

mp: 140–143° C.

MASS: 427 (M+1)

$^1$H-NMR (CDCl$_3$) δ1.38(9H,s), 1.43(3H,t,J=8 Hz), 3.00–3.19(2H,m), 4.11(2H,q,J=8 Hz), 4.40–4.72(3H,m), 4.96–5.10(1H,m), 6.90(1H,br s), 6.92(2H,d,J=8 Hz), 7.13–7.35(5H,m), 7.91(2H,d,J=8 Hz)

Preparation 63

The object compound was obtained according to a similar manner to that of Preparation 2.

mp: 86–91° C.

MASS: 422 (M+1)

$^1$H-NMR (CDCl$_3$) δ1.41(9H,s), 1.42(3H,t,J=8 Hz), 2.92 (3H,s), 3.11(1×1/3H,d,J=10 Hz), 3.18(1×2/3H,d,J=10 Hz), 3.31(1×2/3H,d,J=6 Hz), 3.36(1×1/3H,d,J=6 Hz), 4.05(2H,q, J=8 Hz), 5.00(1H,q,J=8 Hz), 5.60(1H,d,J=8 Hz), 6.91(2H, d,J=8 Hz), 6.99(1H,s), 7.00–7.09(2H,m), 7.13(2H,d,J=8 Hz), 7.19–7.25(3H,m)

Preparation 64

The object compound was obtained according to a similar manner to that of Preparation 3 except that a mixture of trifluoroacetic acid and dichloromethane was used instead of trifluoroacetic acid.

MASS: 322 (M+1)

$^1$H-NMR (CDCl$_3$) δ1.43(3H,t,J=8 Hz), 3.09–3.27(2H,m), 3.12(3H,s), 4.07(2H,q,J=8 Hz), 4.13(1H,t,J=8 Hz), 6.91(2H, d,J=8 Hz), 7.00(1H,s), 7.10(2H,d,J=7 Hz), 7.19(2H,d,J=8 Hz), 7.21–7.31 (3H,m)

Preparation 65

The object compound was obtained according to a similar manner to that of Preparation 28.

amorphous solid

MASS: 411 (M+1)

$^1$H-NMR (CDCl$_3$) δ1.29(3H,t,J=8 Hz), 1.40(9H,s), 2.71 (2H,q,J=8 Hz), 3.00–3.20(2H,m), 4.40–4.53(1H,m), 4.58–4.80(2H,m), 5.00–5.15(1H,m), 6.94(1H,s), 7.12–7.40 (7H,m), 7.88(2H,d,J=8 Hz)

Preparation 66

The object compound was obtained according to a similar manner to that of Preparation 2.

oil

MASS: 406 (M+1)

$^1$H-NMR (CDCl$_3$) δ1.22(3H,t,J=8 Hz), 1.40(9H,s), 2.67 (2H,q,J=8 Hz), 2.93(3H,s), 3.08–3.20(1H,m), 3.30–3.40 (1H,m), 5.00(1H,q,J=8 Hz), 5.69(1H,d,J=8 Hz), 7.00(1H,s), 7.01–7.10(2H,m), 7.10–7.18(2H,m), 7.18–7.32(5H,m)

Preparation 67

The object compound was obtained according to a similar manner to that of Preparation 64.

oil

MASS: 306 (M+1)

$^1$H-NMR (CDCl$_3$) δ1.30(3H,t,J=8 Hz), 2.68(2H,q,J=8 Hz), 3.09–3.28(2H,m), 3.18(3H,s), 4.13(1H,t,J=8 Hz), 7.01 (1H,s), 7.04–7.10(2H,m), 7.12–7.30(7H,m)

Preparation 68

The object compound was obtained according to a similar manner to that of Preparation 28.

Oil

MASS: 447 (M+1)

$^1$H-NMR (CDCl$_3$) δ1.40(9H,s), 3.02(2H,d,J=6 Hz), 3.76 (3H,s), 4.33–4.47(1H,m), 4.50–4.71(2H,m), 4.91–5.30(1H, m), 6.72–6.80(1H,m), 6.81(2H,d,J=8 Hz), 7.11(2H,d,J=8 Hz), 7.30–7.40(1H,m), 7.41–7.48(2H,m), 7.51(1H,d,J=8 Hz)

Preparation 69

The object compound was obtained according to a similar manner to that of Preparation 2.

oil

MASS: 442 (M+1)

$^1$H-NMR (CDCl$_3$) δ1.47(9H,s), 2.86(3H,s), 3.01–3.12 (1H,m), 3.22–3.31(1H,m), 3.73(3H,s), 4.89–5.00(1H,m), 5.61(1H,d,J=8 Hz), 6.73(2H,d,J=8 Hz), 6.97(2H,d,J=8 Hz), 7.00(1H,s), 7.20–7.39(3H,m), 7.44(1H,d,J=8 Hz)

Preparation 70

The object compound was obtained according to a similar manner to that of Preparation 64.

oil

MASS: 342 (M+1)

$^1$H-NMR (CDCl$_3$) δ3.04(3H,s), 3.08–3.17(2H,m), 3.75 (3H,s), 4.11(1H,t,J=8 Hz), 6.80(2H,d,J=8 Hz), 7.00(2H,d, J=8 Hz), 7.01(1H,s), 7.21–7.40(3H,m), 7.47(1H,d,J=7 Hz)

Preparation 71

The object compound was obtained according to a similar manner to that of Preparation 28.

mp: 115–122° C.

MASS: 427 (M+1)

$^1$H-NMR (CDCl$_3$) δ1.42(9H,s), 2.42(3H,s), 3.07(2H,d, J=7 Hz), 3.76(3H,s), 4.38–4.50(1H,m), 4.58–4.77(2H,m), 4.98–5.10(1H,m), 6.81(2H,d,J=8 Hz), 6.87–6.92(1H,m), 7.11(2H,d,J=8 Hz), 7.29(2H,d,J=8 Hz), 7.85(2H,d,J=8 Hz)

Preparation 72

The object compound was obtained according to a similar manner to that of Preparation 2.

oil

MASS: 422 (M+1)

$^1$H-NMR (CDCl$_3$) δ1.42(9H,s), 2.38(3H,s), 2.99(3H,s), 3.01–3.18(1H,m), 3.20–3.30(1H,m), 3.71(3H,s), 4.93(1H,q, J=8 Hz), 5.58(1H,d,J=8 Hz), 6.73(2H,d,J=8 Hz), 6.93(2H, d,J=8 Hz), 7.00(1H,s), 7.11(2H,d,J=7 Hz), 7.20(2H,d,J=7 Hz)

Preparation 73

The object compound was obtained according to a similar manner to that of Preparation 64.

oil

MASS: 322 (M+1)

$^1$H-NMR (CDCl$_3$) δ2.39(3H,s), 3.10(1H,t,J=8 Hz), 3.19 (3H,s), 3.80(3H,s), 4.12(1H,t,J=8 Hz), 6.81(2H,d,J=8 Hz), 7.00(2H,d,J=8 Hz), 7.01(1H,s), 7.12–7.23(5H,m)

Preparation 74

The object compound was obtained according to a similar manner to that of Preparation 28.

mp: 105–108° C.

MASS: 447 (M+1)

$^1$H-NMR (CDCl$_3$) δ1.40(9H,s), 3.06(2H,d,J=7 Hz), 3.79 (3H,s), 4.41(1H,br s), 4.58–4.77(2H,m), 4.99(1H,br s), 6.81 (2H,d,J=8 Hz), 6.83(1H,s), 7.12(2H,d,J=8 Hz), 7.49(2H,d, J=7 Hz), 7.90(2H,d,J=7 Hz)

Preparation 75

The object compound was obtained according to a similar manner to that of Preparation 2.

amorphous solid $^1$H-NMR (CDCl$_3$) δ1.40(9H,s), 2.98–3.13(1H,m), 3.00 (3H,s), 3.21–3.32(1H,m), 3.78(3H,s), 4.90–5.02(1H,m), 5.57(1H,d,J=8 Hz), 6.78(2H,d,J=8 Hz), 6.93(2H,d,J=8 Hz), 7.02(1H,s), 7.18(2H,d,J=8 Hz), 7.38(2H,d,J=8 Hz)

Preparation 76

The object compound was obtained according to a similar manner to that of Preparation 64.

oil $^1$H-NMR (CDCl$_3$) δ3.11(2H,t,J=7 Hz), 3.19(3H,s), 3.80 (3H,s), 4.11(1H,t,J=8 Hz), 6.80(2H,d,J=8 Hz), 7.00(2H,d,J=8 Hz), 7.02(1H,s), 7.20(2H,d,J=8 Hz), 7.38(2H,d,J=8 Hz)

Preparation 77

The object compound was obtained according to a similar manner to that of Preparation 28.

amorphous solid

MASS: 447 (M+1)

$^1$H-NMR (CDCl$_3$) δ1.40(9H,s), 3.07(2H,d,J=6 Hz), 3.73 (3H,s), 4.42(1H,br s), 4.58–4.80(2H,m), 5.01(1H,br s), 6.81 (2H,d,J=8 Hz), 6.84(1H,br s), 7.11(2H,d,J=8 Hz), 7.42(1H, t,J=8 Hz), 7.59(1H,d,J=8 Hz), 7.81(1H,d,J=8 Hz), 7.91(1H, s)

Preparation 78

The object compound was obtained according to a similar manner to that of Preparation 2.

amorphous solid

MASS: 442 (M+1)

$^1$H-NMR (CDCl$_3$) δ1.43(9H,s), 3.00(3H,s), 3.11–3.32 (2H,m), 3.79(3H,s), 4.91–5.03(1H,m), 5.88(1H,br s), 6.78 (2H,d,J=8 Hz), 6.93(2H,d,J=8 Hz), 7.03–7.19(2H,m), 7.21 (1H,s), 7.30–7.40(2H,m)

Preparation 79

The object compound was obtained according to a similar manner to that of Preparation 64.

oil

MASS: 342 (M+1)

$^1$H-NMR (CDCl$_3$) δ3.07–3.20(2H,m), 3.18(3H,s), 3.78 (3H,s), 4.20(1H,t,J=8 Hz), 6.80(2H,d,J=8 Hz), 6.99(2H,d, J=8 Hz), 7.09(1H,s), 7.11–7.21(1H,m), 7.28(1H,s), 7.30–7.40(2H,m)

Preparation 80

The object compound was obtained according to a similar manner to that of Preparation 28.

mp: 120–123° C.

MASS: 431 (M+1)

$^1$H-NMR (CDCl$_3$) δ1.43(9H,s), 3.08(2H,d,J=8 Hz), 3.76 (3H,s), 4.42(1H,br s), 4.58–4.78(2H,m), 5.00(1H,br s), 6.82 (2H,d,J=8 Hz), 6.87(1H,s), 7.10–7.22(4H,m), 8.00(2H,t,J=7 Hz)

Preparation 81

The object compound was obtained according to a similar manner to that of Preparation 2.

amorphous solid

MASS: 426 (M+1)

$^1$H-NMR (CDCl$_3$) δ1.41(9H,s), 2.99(3H,s), 3.01–3.32 (2H,m), 3.74(3H,s), 4.90–5.02(1H,m), 5.70(1H,d,J=7 Hz), 6.76(2H,d,J=8 Hz), 6.95(2H,d,J=8 Hz), 7.01(1H,s), 7.03–7.16(2H,m), 7.16–7.23(2H,m)

Preparation 82

The object compound was obtained according to a similar manner to that of Preparation 64.

oil

MASS: 326 (M+1)

$^1$H-NMR (CDCl$_3$) δ3.08–3.22(2H,m), 3.18(3H,s), 3.80 (3H,s), 4.18(1H,t,J=8 Hz), 6.80(2H,d,J=8 Hz), 6.99(2H,d, J=8 Hz), 7.00(1H,s), 7.09(2H,t,J=8 Hz), 7.20–7.30(2H,m)

Preparation 83

The object compound was obtained according to a similar manner to that of Preparation 28.

mp: 131–134° C.

MASS: 457 (M+1)

$^1$H-NMR (CDCl$_3$) δ1.43(9H,s), 1.47(3H,t,J=8 Hz), 3.05 (2H,d,J=8 Hz), 3.77(3H,s), 4.10(2H,q,J=8 Hz), 4.41(1H,br s), 4.51–4.73(2H,m), 5.01(1H,br s), 6.80(2H,d,J=8 Hz), 6.90 (1H,br s), 6.92(2H,d,J=8 Hz), 7.11(2H,d,J=8 Hz), 7.91(2H, d,J=8 Hz)

Preparation 84

The object compound was obtained according to a similar manner to that of Preparation 2.

solid

MASS: 452 (M+1)

$^1$H-NMR (CDCl$_3$) δ1.41(9H,s), 1.44(3H,t,J=8 Hz), 2.99 (3H,s), 3.01–3.13(1H,m), 3.20–3.31(1H,m), 3.78(3H,s), 4.03(2H,q,J=8 Hz), 4.88–4.98(1H,m), 5.58(1H,q,J=8 Hz), 6.78(2H,d,J=8 Hz), 6.88–7.00(5H,m), 7.12(2H,d,J=8 Hz)

Preparation 85

The object compound was obtained according to a similar manner to that of Preparation 64.

oil

MASS: 352 (M+1)

$^1$H-NMR (CDCl$_3$) δ1.43(3H,t,J=8 Hz), 3.02–3.17(2H,m), 3.18(3H,s), 3.75(3H,s), 4.00–4.18(1H,m), 4.05(2H,q,J=8 Hz), 6.80(2H,d,J=8 Hz), 6.91(2H,d,J=8 Hz), 6.98(1H,s), 7.00(2H,d,J=8 Hz), 7.19(2H,d,J=8 Hz)

Preparation 86

A solution of potassium tert-butoxide (4.2 g) in anhydrous tetrahydrofuran (70 ml) was cooled under nitrogen atmosphere to −70° C., and a solution of the starting compound (10 g) in anhydrous tetrahydrofuran (35 ml) was added while maintaining the reaction temperature at −70° C. After 30 minutes, this solution was added dropwise to a solution of 4-bromobenzoyl chloride (8.21 g) in anhydrous tetrahydrofuran (24 ml) with stirring while cooling at −70° C. on a cooling bath. The reaction mixture was stirred at −70° C. for 1 hour and quenched with 3N-hydrochloric acid (100 ml). The cooling bath was removed and the reaction mixture was concentrated to dryness under reduced pressure. The residue was dissolved in water (15 ml) and extracted with diethyl ether (twice). The aqueous layer was concentrated in vacuo, and the residue was dissolved in anhydrous methanol. The precipitated white solid (KCl) was removed by filtration. The filtrate was concentrated in vacuo and the residue was crystallized from tetrahydrofuran/diethyl ether to give the object compound as an off-white solid.

mp: 183–188° C.

MASS: 286 (M+H)$^+$ $^1$H-NMR (DMSO-d$_6$, δ) 1.03(3H,t,J=7.0 Hz), 4.13(2H,q, J=7.0 Hz), 6.24(1H,s), 7.86(2H,d,J=7.5 Hz), 8.09(2H,d,J= 7.5 Hz), 9.10(2H,br s),

Preparation 87

The object compound was obtained according to a similar manner to that of Preparation 28.

pale yellow amorphous solid

MASS: 531 (M−H)$^+$ $^1$H-NMR (CDCl$_3$, δ) 1.14(3H,t,J=7.0 Hz), 1.40(9H,s), 2.97–3.18(2H,m), 4.16(2H,q,J=7.0 Hz), 4.49(1H,m), 4.96 (1H,m), 6.03(1H×3/7,d,J=7.0 Hz), 6.06(1H×4/7,d,J=7.0 Hz), 7.14–7.31(6H,m), 7.64(2H,d,J=7.5 Hz), 7.95(2H×3/7, d,J=7.5 Hz), 7.97(2H×4/7,d,J=7.5 Hz)

Preparation 88

The object compound was obtained according to a similar manner to that of Preparation 2.

pale yellow amorphous solid

MASS: 528 (M+H)$^+$ $^1$H-NMR (CDCl$_3$, δ) 1.18(3H,t,J=7.0 Hz), 1.41(9H,s), 2.69(3H,s), 3.17(1H,dd,J=13.5 and 9.0 Hz), 3.37(1H,dd,J= 13.5 and 7.0 Hz), 4.23(2H,q,J=7.0 Hz), 4.98(1H,m), 5.74 (1H,d,J=7.5 Hz), 6.97–7.08(4H,m), 7.19–7.27(3H,m), 7.55 (2H,d,J=7.5 Hz)

Preparation 89

The object compound was obtained according to a similar manner to that of Preparation 3.

pale yellow oil
MASS: 428 (M+H)$^+$
$^1$H-NMR (CDCl$_3$, δ) 1.20(3H,t,J=7.0 Hz), 2.97(3H,s), 3.22(2H,d,J=7.0 Hz), 4.19(1H,t,J=7.0 Hz), 4.25(2H,q,J=7.0 Hz), 7.05–7.15(4H,m), 7.21–7.33(3H,m), 7.57(2H,d,J=7.5 Hz)

Preparation 90

The object compound was obtained according to a similar manner to that of Preparation 28.

pale yellow solid
mp: 148–152.5° C.
MASS: 383 (M+H)$^+$
$^1$H-NMR (CDCl$_3$, δ) 1.41(9H,s), 3.12(2H,d,J=7.0 Hz), 4.49(1H,m), 4.65(1H,dd,J=20.5 and 5.5 Hz), 4.75(1H,dd,J=20.5 and 5.5 Hz), 5.03(1H,m), 6.89(1H,m), 7.28–7.32(5H,m), 7.50(2H,t,J=7.5 Hz), 7.62(1H,t,J=7.5 Hz), 7.94(2H,d,J=7.5 Hz)

Preparation 91

The object compound was obtained according to a similar manner to that of Preparation 2.

brown amorphous solid
MASS: 378 (M+H)$^+$
$^1$H-NMR (CDCl$_3$, δ) 1.42(9H,s), 2.97(3H,s), 3.14(1H,dd, J=13.5 and 9.0 Hz), 3.35(1H,dd,J=13.5 and 7.0 Hz), 5.01 (1H,m), 5.59(1H,d,J=7.5 Hz), 7.01–7.08(2H,m), 7.03(1H,s), 7.17–7.29(5H,m), 7.32–7.44(3H,m)

Preparation 92

The object compound was obtained according to a similar manner to that of Preparation 3.

brown oil
MASS: 278 (M+H)$^+$
$^1$H-NMR (CDCl$_3$, δ) 3.14(1H,dd,J=13.5 and 7.5 Hz), 3.18(3H,s), 3.21(1H,dd,J=13.5 and 7.5 Hz), 4.15(1H,t,J=7.5 Hz), 7.05(1H,s), 7.09(2H,d,J=7.5 Hz), 7.19–7.44(8H,m)

Preparation 93

The object compound was obtained according to a similar manner to that of Preparation 28.

MASS (ESI) (m/z): 503, 505 (M–H)$^-$
$^1$H-NMR (CDCl$_3$,300 MHz) δ1.38(3H,t,J=7 Hz), 1.41 (9H,s), 3.04(2H,d,J=7 Hz), 3.98(2H,q,J=7 Hz), 4.32–4.49 (1H,m), 4.53–4.77(2H,m), 4.99(1H,br d,J=8 Hz), 6.80(2H, d,J=8 Hz), 6.83(1H,br s), 7.10(2H,d,J=8 Hz), 7.62(2H,d,J=8 Hz), 7.80(2H,d,J=8 Hz)

Preparation 94

The object compound was obtained according to a similar manner to that of Preparation 2.

MASS (ESI) (m/z): 500, 502 (M+H)$^+$
$^1$H-NMR (CDCl$_3$,300 MHz) δ1.39(3H,t,J=7 Hz), 1.41 (9H,s), 2.99(3H,s), 3.05(1H,dd,J=13 and 9 Hz), 3.25(1H,dd, J=13 and 5 Hz), 3.98(2H,q,J=7 Hz), 4.86–5.02(1H,m), 5.56 (1H,br d,J=8 Hz), 6.73(2H,d,J=8 Hz), 6.91(2H,d,J=8 Hz), 7.01(1H,s), 7.09(2H,d,J=8 Hz), 7.51(2H,d,J=8 Hz)

Preparation 95

The object compound was obtained according to a similar manner to that of Preparation 9.

MASS (ESI) (m/z): 400, 402 (M+H)$^+$
$^1$H-NMR (CDCl$_3$,300 MHz) δ1.40(3H,t,J=7 Hz), 3.00–3.18(2H,m), 3.19(3H,s), 4.00(2H,q,J=7 Hz), 4.10(1H, t,J=7 Hz), 6.80(2H,d,J=8 Hz), 6.96(2H,d,J=8 Hz), 7.04(1H, s), 7.15(2H,d,J=8 Hz), 7.54(2H,d,J=8 Hz)

Preparation 96

The object compound was obtained according to a similar manner to that of Preparation 28.

MASS (ESI) (m/z): 491, 493 (M+H)$^+$
$^1$H-NMR (CDCl$_3$,300 MHz) δ1.41(9H,s), 2.92–3.18(2H, m), 3.87(3H,s), 4.40–4.53(1H,m), 4.53–4.78(2H,m), 5.02 (1H,br d,J=8 Hz), 6.95(2H,d,J=8 Hz), 6.98(1H,br s), 7.09 (2H,d,J=8 Hz), 7.40(2H,d,J=8 Hz), 7.93(2H,d,J=8 Hz)

Preparation 97

The object compound was obtained according to a similar manner to that of Preparation 2.

MASS (ESI) (m/z): 486, 488 (M+H)$^+$
$^1$H-NMR (CDCl$_3$,300 MHz) δ1.40(9H,s), 3.09(3H,s), 3.10–3.31(2H,m), 3.83(3H,s), 4.91–5.06(1H,m), 5.48(1H,br d,J=8 Hz), 6.88–7.01(5H,m), 7.17(2H,d,J=8 Hz), 7.35(2H, d,J=8 Hz)

Preparation 98

The object compound was obtained according to a similar manner to that of Preparation 9.

MASS (ESI) (m/z): 386, 388 (M+H)$^+$
$^1$H-NMR (CDCl$_3$,300 MHz) δ3.02–3.25(2H,m), 3.23(3H, s), 3.83(3H,s), 4.12(1H,t,J=7 Hz), 6.89–7.02(5H,m), 7.20 (2H,d,J=8 Hz), 7.38(2H,d,J=8 Hz)

Preparation 99

The object compound was obtained according to a similar manner to that of Preparation 28.

MASS (ESI) (m/z): 455 (M–H)$^-$
$^1$H-NMR (CDCl$_3$,300 MHz) δ1.39(3H,t,J=7 Hz), 1.42 (9H,s), 2.96–3.12(2H,m), 3.88(3H,s), 3.98(2H,q,J=7 Hz), 4.33–4.51(1H,m), 4.52–4.79(2H,m), 4.93–5.11(1H,m), 6.81 (2H,d,J=8 Hz), 6.92(1H,br s), 6.95(2H,d,J=8 Hz), 7.10(2H, d,J=8 Hz), 7.92(2H,d,J=8 Hz)

Preparation 100

The object compound was obtained according to a similar manner to that of Preparation 2.

MASS (ESI) (m/z): 452 (M+H)$^+$
$^1$H-NMR (CDCl$_3$,300 MHz) δ1.39(3H,t,J=7 Hz), 1.41 (9H,s), 2.97(3H,s), 3.00–3.31(2H,m), 3.81(3H,s), 3.98(2H, q,J=7 Hz), 4.86–5.01(1H,m), 5.62(1H,br d,J=8 Hz), 6.74 (2H,d,J=8 Hz), 6.85–6.95(4H,m), 6.96(1H,s), 7.15(2H,d,J=8 Hz)

Preparation 101

The object compound was obtained according to a similar manner to that of Preparation 9.

MASS (ESI) (m/z): 352 (M+H)$^+$
$^1$H-NMR (CDCl$_3$,300 MHz) δ1.40(3H,t,J=7 Hz), 3.00–3.19(2H,m), 3.17(3H,s), 3.82(3H,s), 4.00(2H,q,J=7 Hz), 4.10(1H,t,J=7 Hz), 6.80(2H,d,J=8 Hz), 6.89–7.02(5H, m), 7.20(2H,d,J=8 Hz)

Preparation 102

The object compound was obtained according to a similar manner to that of Preparation 28.

MASS (ESI) (m/z): 441 (M–H)$^-$
$^1$H-NMR (CDCl$_3$,300 MHz) δ1.42(9H,s), 3.06(2H,d,J=7 Hz), 3.76(3H,s), 3.88(3H,s), 4.34–4.52(1H,m), 4.54–4.79 (2H,m), 4.91–5.10(1H,m), 6.82(2H,d,J=8 Hz), 6.91(1H,br s), 6.96(2H,d,J=8 Hz), 7.12(2H,d,J=8 Hz), 7.93(2H,d,J=8 Hz)

Preparation 103

The object compound was obtained according to a similar manner to that of Preparation 2.

MASS (ESI) (m/z): 438 (M+H)$^+$
$^1$H-NMR (CDCl$_3$,300 MHz) δ1.41(9H,s), 2.98(3H,s), 3.01–3.31(2H,m), 3.76(3H,s), 3.81(3H,s), 4.88–5.00(1H,m), 5.59(1H,br d,J=8 Hz), 6.77(2H,d,J=8 Hz), 6.87–7.00(5H,m), 7.14(2H,d,J=8 Hz)

Preparation 104

The object compound was obtained according to a similar manner to that of Preparation 9.

MASS (ESI) (m/z): 338 (M+H)$^{30}$
$^1$H-NMR (CDCl$_3$,300 MHz) δ3.01–3.20(2H,m), 3.18(3H, s), 3.78(3H,s), 3.83(3H,s), 4.10(1H,t,J=7 Hz), 6.81(2H,d, J=8 Hz), 6.89–7.05(5H,m), 7.20(2H,d,J=8 Hz)

EXAMPLE 1

To an ice-cooled solution of the starting compound (76 mg), indole-2-carboxylic acid (66 mg) and 1-hydroxybenzotriazole (58 mg) in dichloromethane (1 ml) was added 1-(3-dimethylaminopropyl)-3-ethylcarbodiimide hydrochloride (96 mg). The mixture was stirred at room temperature for 12 hours. A saturated aqueous sodium hydrogencarbonate solution was added to the mixture, and then the mixture was extracted three times with chloroform. The organic layer was washed with brine, dried over magnesium sulfate, filtered and concentrated. The residue was purified by column chromatography (silica gel, chloroform/methanol=70/1) to give the object compound as white powder (128 mg).

MASS (ESI) (m/z): 331 (M+H)$^+$ $^1$H-NMR (CDCl$_3$,300 MHz) δ: 3.62(3H,s), 4.80(2H,d,J=5 Hz), 6.98–7.92(12H,m), 9.50(1H,br s)

EXAMPLE 2

The object compound was obtained according to a similar manner to that of Example 1.

MASS (ESI) (m/z): 332 (M+H)$^+$ $^1$H-NMR (CDCl$_3$,300 MHz) δ: 3.64(3H,s), 4.80(2H,d,J=5 Hz), 7.05(1H,s), 7.20–7.72(12H,m)

EXAMPLE 3

The object compound was obtained according to a similar manner to that of Example 1.

MASS (ESI) (m/z): 493 (M+H)$^+$ $^1$H-NMR (CDCl$_3$,300 MHz) δ: 1.06(3H,t,J=7 Hz), 2.81 (3H,s), 3.42–3.65(2H,m), 4.17(2H,q,J=7 Hz), 5.48–5.64 (1H,m), 6.88–7.63(15H,m), 8.41(1H,br s), 9.50(1H,br s)

EXAMPLE 4

The object compound was obtained according to a similar manner to that of Example 1.

MASS (ESI) (m/z): 494 (M+H)$^+$ $^1$H-NMR (CDCl$_3$,300 MHz) δ: 1.12(3H,t,J=7 Hz), 2.81 (3H,s), 3.32–3.56(2H,m), 4.22(2H,q,J=7 Hz), 5.48–5.62 (1H,m), 7.05–7.70(15H,m), 7.82(1H,br d,J=8 Hz)

EXAMPLE 5

The object compound was obtained according to a similar manner to that of Example 1.

MASS (ESI) (m/z): 451 (M+H)$^+$ $^1$H-NMR (CDCl$_3$,300 MHz) δ: 3.09(3H,s), 3.22–3.50 (2H,m), 3.72(3H,s), 5.50–5.64(1H,m), 6.72(2H,d,J=8 Hz), 6.96(2H,d,J=8 Hz), 7.00–7.65(11H,m), 8.13(1H,br d,J=8 Hz), 10.50(1H,br s)

EXAMPLE 6

The object compound was obtained according to a similar manner to that of Example 1.

MASS (ESI) (m/z): 452 (M+H)$^+$ $^1$H-NMR (CDCl$_3$,300 MHz) δ: 3.06(3H,s), 3.17–3.48 (2H,m), 3.75(3H,s), 5.41–5.56(1H,m), 6.77(2H,d,J=8 Hz), 6.98(2H,d,J=8 Hz), 7.10(1H,s), 7.18–7.80(11H,m)

EXAMPLE 7

The object compound was obtained according to a similar manner to that of Example 1.

MASS (ESI) (m/z): 529, 531 (M+H)$^+$ $^1$H-NMR (CDCl$_3$,300 MHz) δ: 3.08(3H,s), 3.22–3.50 (2H,m), 3.72(3H,s), 5.50–5.64(1H,m), 6.72(2H,d,J=8 Hz), 6.98(2H,d,J=8 Hz), 7.00–7.65(10H,m), 8.11(1H,br d,J=8 Hz), 9.95(1H,br s)

EXAMPLE 8

The object compound was obtained according to a similar manner to that of Example 1.

MASS (ESI) (m/z): 530, 532 (M+H)$^+$ $^1$H-NMR (CDCl$_3$,300 MHz) δ: 3.06(3H,s), 3.15–3.48 (2H,m), 3.75(3H,s), 5.40–5.55(1H,m), 6.77(2H,d,J=8 Hz), 6.98(2H,d,J=8 Hz), 7.05–7.75(11H,m)

EXAMPLE 9

The object compound was obtained according to a similar manner to that of Example 1.

MASS (ESI) (m/z): 467 (M+H)$^+$ $^1$H-NMR (CDCl$_3$,300 MHz) δ: 2.50(3H,s), 3.01(3H,s), 3.22–3.56(2H,m), 5.51–5.66(1H,m), 6.98–7.68(15H,m), 7.95(1H,br d,J=8 Hz), 9.60(1H,br s)

EXAMPLE 10

The object compound was obtained according to a similar manner to that of Example 1.

MASS (ESI) (m/z): 468 (M+H)$^+$ $^1$H-NMR (CDCl$_3$,300 MHz) δ: 2.50(3H,s), 3.00(3H,s), 3.22–3.55(2H,m), 5.46–5.60(1H,m), 7.02–7.80(16H,m)

EXAMPLE 11

The object compound was obtained according to a similar manner to that of Example 1.

MASS (ESI) (m/z): 533, 535 (M+H)$^+$ $^1$H-NMR (CDCl$_3$,300 MHz) δ: 3.18(3H,s), 3.30–3.48 (2H,m), 5.52–5.68(1H,m), 6.93–8.00(15H,m), 9.78(1H,br s)

EXAMPLE 12

The object compound was obtained according to a similar manner to that of Example 1.

MASS (ESI) (m/z): 534, 536 (M+H)$^+$ $^1$H-NMR (CDCl$_3$,300 MHz) δ: 3.18(3H,s), 3.26–3.49 (2H,m), 5.47–5.61(1H,m), 6.98–7.70(15H,m)

EXAMPLE 13

The object compound was obtained according to a similar manner to that of Example 1.

amorphous solid

MASS (ESI) (m/z): 499 (M+H)$^+$ $^1$H-NMR (CDCl$_3$+CD$_3$OD,300 MHz) δ: 2.88(3H,s), 3.00 (1×1/3H,d,J=8 Hz), 3.03(1×2/3H,d,J=8 Hz), 3.11(1×2/3H,d, J=4 Hz), 3.16(1×1/3H,d,J=4 Hz), 5.30(1H,q,J=6 Hz), 6.70–6.90(6H,m), 6.90–7.04(5H,m), 7.10(1H,s), 7.16(1H,d, J=8 Hz), 7.26(2H,d,J=8 Hz), 7.40(1H,d,J=8 Hz)

EXAMPLE 14

The object compound was obtained according to a similar manner to that of Example 1.

amorphous solid

MASS (ESI) (m/z): 500 (M+H)$^+$ $^1$H-NMR (CDCl$_3$,300 MHz) δ: 2.99(3H,s), 3.30(1×1/3H, d,J=8 Hz), 3.32(1×2/3H,d,J=8 Hz), 3.49(1×2/3H,d, J=4 Hz), 3.51(1×1/3H,d,J=4 Hz), 5.49–5.60(1H,m), 7.00–7.19(5H, m), 7.19–7.32(4H,m), 7.40(1H,t,J=8 Hz), 7.49(1H,s), 7.52 (3H,d,J=8 Hz), 7.64(1H,d,J=8 Hz), 7.93(1H,d,J=8 Hz)

EXAMPLE 15

The object compound was obtained according to a similar manner to that of Example 1.

amorphous solid

MASS (ESI) (m/z): 455 (M+H)$^+$ $^1$H-NMR (CDCl$_3$,300 MHz) δ: 3.01(3H,s), 3.32(1×1/3H, d,J=8 Hz), 3.39(1×2/3H,d,J=8 Hz), 3.49(1×2/3H,d,J=4 Hz), 3.52(1×1/3H,d,J=4 Hz), 5.60(1H,q,J=8 Hz), 7.00–7.19(7H, m), 7.19–7.30(4H,m), 7.30–7.43(3H,m), 7.61(1H,d,J=8 Hz), 8.17(1H,d,J=8 Hz), 9.88(1H,s)

EXAMPLE 16

The object compound was obtained according to a similar manner to that of Example 1.

amorphous solid

MASS (ESI) (m/z): 456 (M+H)$^+$ $^1$H-NMR (CDCl$_3$,300 MHz) δ: 2.99(3H,s), 3.29(1×1/3H, d,J=8 Hz), 3.32(1×2/3H,d,J=8 Hz), 3.49(1×2/3H,d,J=4 Hz), 3.52(1×1/3H,d,J=4 Hz), 5.48–5.60(1H,m), 7.03–7.11(3H, m), 7.15(2H,d,J=8 Hz), 7.20–7.31(4H,m), 7.38(2H,d,J=8 Hz), 7.41–7.58(3H,m), 7.67(1H,d,J=8 Hz), 7.80(1H,d,J=8 Hz)

EXAMPLE 17

The object compound was obtained according to a similar manner to that of Example 1.

mp: 145–150° C.

MASS (ESI) (m/z): 435 (M+H)$^+$ $^1$H-NMR (CDCl$_3$,300 MHz) δ: 2.31(3H,s), 3.02(3H,s), 3.33–3.57(2H,m), 5.60–5.73(1H,m), 7.00–7.12(7H,m), 7.12–7.22(6H,m), 7.36(1H,d,J=8 Hz), 7.59(1H,d,J=8 Hz), 8.57(1H,d,J=8 Hz)

EXAMPLE 18

The object compound was obtained according to a similar manner to that of Example 1.

amorphous solid

MASS (ESI) (m/z): 436 (M+H)$^+$ $^1$H-NMR (CDCl$_3$,300 MHz) δ: 2.38(3H,s), 3.00(3H,s), 3.30(1×1/3H,d,J=8 Hz), 3.38(1'2/3H,d,J=8 Hz), 3.50(1×2/ 3H,d,J=4 Hz), 3.52(1×1/3H,d,J=4 Hz), 5.48–5.62(1H,m), 7.02–7.14(5H,m), 7.16–7.33(6H,m), 7.35–7.55(3H,m), 7.65 (1H,d,J=8 Hz), 7.91(1H,d,J=8 Hz)

EXAMPLE 19

The object compound was obtained according to a similar manner to that of Example 1.

amorphous solid

MASS (ESI) (m/z): 455 (M+H)$^+$ $^1$H-NMR (CDCl$_3$,300 MHz) δ: 3.18(3H,s), 3.40–3.50 (2H,m), 5.70(1H,q,J=8 Hz), 6.98–7.29(10H,m), 7.30–7.42 (4H,m), 7.59(1H,d,J=8 Hz), 8.60(1H,d,J=8 Hz)

EXAMPLE 20

The object compound was obtained according to a similar manner to that of Example 1.

amorphous solid

MASS (ESI) (m/z): 456 (M+H)$^+$ $^1$H-NMR (CDCl$_3$,300 MHz) δ: 3.19(3H,s), 3.30–3.51 (2H,m), 5.49–5.60(1H,m), 7.04(2H,d,J=8 Hz), 7.10(1H,s), 7.14–7.31(5H,m), 7.31–7.52(6H,m), 7.64(1H,d,J=8 Hz), 7.78(1H,d,J=8 Hz)

EXAMPLE 21

The object compound was obtained according to a similar manner to that of Example 1.

colorless solid mp: 223–226° C.

MASS (ESI) (m/z): 435 (M+H)$^+$ $^1$H-NMR (CDCl$_3$,300 MHz) δ: 2.23(3H,s), 3.23–3.40 (2H,m), 4.77(1H,d,J=16.0 Hz), 4.83(1H,d,J=16.0 Hz), 5.60 (1H,q,J=7.5 Hz), 6.70(1H,s), 6.78(2H,d,J=7.5 Hz), 6.93(1H, s), 6.97–7.29(10H,m), 7.37(1H,d,J=7.5 Hz), 7.58(1H,d,J= 7.5 Hz), 7.62(1H,d,J=7.5 Hz), 9.47(1H,br s)

EXAMPLE 22

The object compound was obtained according to a similar manner to that of Example 1.

pale yellow amorphous solid

MASS (ESI) (m/z): 421 (M+H)$^+$ $^1$H-NMR (CDCl$_3$, δ) 3.00(3H,s), 3.30(1H,dd,J=12.0, 8.5 Hz), 3.49(1H,dd,J=12.0, 5.5 Hz), 5.57(1H,m), 6.99–7.43 (15H,m), 7.63(1H,d,J=7.5 Hz), 7.76(1H,d,J=7.5 Hz), 9.41 (1H,s)

EXAMPLE 23

The object compound was obtained according to a similar manner to that of Example 1.

colorless solid mp: 234–239° C.

MASS (ESI) (m/z): 345 (M+H)$^+$ $^1$H-NMR (CDCl$_3$–CD$_3$OD, δ) 3.17(3H,s), 3.20(1H,dd,J= 13.5, 9.0 Hz), 3.34(1H,dd,J=13.5, 5.5 Hz), 5.49(1H,dd,J= 9.0, 5.5 Hz), 6.66(1H,s), 6.97–7.03(3H,m), 7.13(1H,t,J=7.5 Hz), 7.18–7.31(5H,m), 7.41(1H,d,J=7.5 Hz), 7.68(1H,d,J= 7.5 Hz)

EXAMPLE 24

The object compound was obtained according to a similar manner to that of Example 1.

colorless solid mp: 251–256° C.

MASS (ESI) (m/z): 331 (M+H)$^+$ $^1$H-NMR (CDCl$_3$–CD$_3$OD, δ) 3.31(2H,d,J=7.5 Hz), 5.39 (1H,t,J=7.5 Hz), 6.90(2H,s), 7.02–7.31(8H,m), 7.39(1H,d, J=7.5 Hz), 7.64(1H,d,J=7.5 Hz)

EXAMPLE 25

The object compound was obtained according to a similar manner to that of Example 1.

off-white solid mp: 202–206° C.

MASS (ESI) (m/z): 472 (M+H)$^+$

¹H-NMR (CDCl₃, δ) 3.10(3H,s), 3.35(1H,dd,J=13.5, 8.5 Hz), 3.53(1H,dd,J=13.5, 5.5 Hz), 5.61(1H,m), 7.03(1H,s), 7.09–7.17(3H,m), 7.20(1H,s), 7.23–7.32(4H,m), 7.38–7.46 (2H,m), 7.56(1H,dd,J=7.5, 2.5 Hz), 7.65(1H,d,J=7.5 Hz), 7.67(1H,s), 7.75(1H,d,J=7.5 Hz), 8.11(2H,d,J=7.5 Hz), 8.93 (1H,d,J=5.5 Hz), 9.40(1H,s)

EXAMPLE 26

The object compound was obtained according to a similar manner to that of Example 1.

off-white amorphous solid

MASS (ESI) (m/z): 472 (M+H)⁺

¹H-NMR (CDCl₃, δ) 3.07(3H,s), 3.33(1H,dd,J=13.5, 10.0 Hz), 3.55(1H,dd,J=13.5, 5.5 Hz), 5.62(1H,m), 7.03(1H,s), 7.07–7.18(3H,m), 7.22–7.33(5H,m), 7.41(1H,d,J=7.5 Hz), 7.60(1H,t,J=7.5 Hz), 7.69(2H,t,J=7.5 Hz), 7.77(1H,t,J=7.5 Hz), 7.82(1H,d,J=7.5 Hz), 8.02(1H,d,J=1.0 Hz), 8.13(1H,d, J=7.5 Hz), 8.80(1H,d,J=1.0 Hz), 9.37(1H,br s)

EXAMPLE 27

The object compound was obtained according to a similar manner to that of Example 1.

pale yellow amorphous solid

MASS (ESI) (m/z): 451 (M+H)⁺

¹H-NMR (CDCl₃, δ) 3.08(3H,s), 3.38(1H,dd,J=13.5, 9.0 Hz), 3.50(1H,dd,J=13.5, 6.0 Hz), 3.82(3H,s), 5.64(1H,m), 6.92(2H,d,J=7.5 Hz), 7.03–8.14(14H,m), 9.63(1H,br s)

EXAMPLE 28

The object compound was obtained according to a similar manner to that of Example 1.

colorless solid mp: 221–230.5° C.

MASS (ESI) (m/z): 451 (M+H)⁺

¹H-NMR (CDCl₃, δ) 3.32(2H,m), 3.70(3H,s), 4.74(2H,s), 5.62(1H,m), 6.67(1H,s), 6.71(2H,d,J=7.5 Hz), 6.82(2H,d,J= 7.5 Hz), 6.93(1H,d,J=1.0 Hz), 6.99–7.30(8H,m), 7.37(1H, d,J=7.5 Hz), 7.56–7.65(2H,m), 9.50(1H,s)

EXAMPLE 29

The object compound was obtained according to a similar manner to that of Example 1.

off-white solid mp: 192.5–198° C.

MASS (ESI) (m/z): 405 (M+H)⁺

¹H-NMR (CDCl₃, δ) 2.10(3H,s), 2.30–2.75(4H,m), 3.66 (3H,s), 5.71(1H,q,J=7.5 Hz), 6.95–7.04(2H,m), 7.11(1H,t, J=7.5 Hz), 7.21–7.47(7H,m), 7.58(1H,d,J=7.5 Hz), 7.63(1H, d,J=7.5 Hz), 9.54(1H,s)

EXAMPLE 30

The object compound was obtained according to a similar manner to that of Example 1.

MASS (ESI) (m/z): 532, 534 (M+H)⁺

¹H-NMR (CDCl₃,300 MHz) δ: 3.27–3.50(2H,m), 3.74 (3H,s), 5.69–5.83(1H,m), 6.79(2H,d,J=8 Hz), 6.88(1H,s), 7.04(2H,d,J=8 Hz), 7.08–7.69(9H,m), 7.88(1H,s), 9.46(1H, br s)

EXAMPLE 31

The object compound was obtained according to a similar manner to that of Example 1.

MASS (ESI) (m/z): 533, 535 (M+H)⁺

¹H-NMR (CDCl₃,300 MHz) δ: 3.30–3.49(2H,m), 3.75 (3H,s), 5.68–5.82(1H,m), 6.79(2H,d,J=8 Hz), 7.09(2H,d,J=8 Hz), 7.20–7.80(10H,m), 7.89(1H,s)

EXAMPLE 32

The object compound was obtained according to a similar manner to that of Example 1.

mp: 178–182° C.

MASS: 465 (M+1)

¹H-NMR (CDCl₃) δ: 1.42(3H,t,J=8 Hz), 3.02(3H,s), 3.36–3.59(2H,m), 4.02(2H,q,J=8 Hz), 5.67(1H,q,J=8 Hz), 6.89(2H,d,J=8 Hz), 7.01(1H,s), 7.03–7.13(6H,m), 7.17–7.30 (4H,m), 7.38(1H,d,J=8 Hz), 7.60(1H,d,J=8 Hz), 8.48(1H,d, J=8 Hz)

EXAMPLE 33

The object compound was obtained according to a similar manner to that of Example 1.

amorphous solid

MASS: 466 (M+1)

¹H-NMR (CDCl₃) δ: 1.42(3H,t,J=8 Hz), 2.95(3H,s), 3.23–3.37(1H,m), 3.43–3.53(1H,m), 4.02(2H,q,J=8 Hz), 5.45–5.58(1H,m), 6.90(2H,d,J=8 Hz), 7.01(1H,s), 7.03–7.18 (4H,m), 7.19–7.31(4H,m), 7.40(1H,t,J=8 Hz), 7.43(1H,s), 7.51(1H,d,J=8 Hz), 7.63(1H,d,J=8 Hz), 7.81(1H,d,J=8 Hz)

EXAMPLE 34

The object compound was obtained according to a similar manner to that of Example 1.

mp: 174–178° C.

MASS: 449 (M+1)

¹H-NMR (CDCl₃) δ: 1.28(3H,t,J=8 Hz), 2.69(2H,q,J=8 Hz), 3.08(3H,s), 3.40–3.60(2H,m), 5.68–5.80(1H,m), 7.02–7.19(7H,m), 7.19–7.30(6H,m), 7.40(1H,d,J=8 Hz), 7.61(1H,d,J=8 Hz), 8.69(1H,d,J=8 Hz)

EXAMPLE 35

The object compound was obtained according to a similar manner to that of Example 1.

amorphous solid

MASS: 450 (M+1)

¹H-NMR (CDCl₃) δ: 1.24(3H,t,J=8 Hz), 2.69(2H,t,J=8 Hz), 3.00(3H,s), 3.25–3.38(1H,m), 3.43–3.57(1H,m), 5.48–5.60(1H,m), 7.00–7.19(5H,m), 7.19–7.32(6H,m), 7.40 (1H,t,J=8 Hz), 7.45(1H,s), 7.51(1H,d,J=8 Hz), 7.63(1H,d, J=8 Hz), 7.81(1H,d,J=8 Hz)

EXAMPLE 36

The object compound was obtained according to a similar manner to that of Example 1.

amorphous solid

MASS: 485 (M+1)

¹H-NMR (CDCl₃) δ: 2.93(3H,s), 3.30–3.50(2H,m), 3.70 (3H,s), 5.53–5.63(1H,m), 6.71(2H,d,J=8 Hz), 6.98(2H,d,J=8 Hz), 7.00–7.12(3H,m), 7.16–7.40(5H,m), 7.42(1H,d,J=8 Hz), 7.60(1H,d,J=8 Hz), 8.40(1H,d,J=8 Hz)

EXAMPLE 37

The object compound was obtained according to a similar manner to that of Example 1.

amorphous solid

MASS: 465 (M+1)

$^1$H-NMR (CDCl$_3$) δ: 2.39(3H,s), 3.10(3H,s), 3.30–3.50 (2H,m), 3.70(3H,s), 5.61(1H,q,J=8 Hz), 6.70(2H,d,J=8 Hz), 6.99(2H,d,J=8 Hz), 7.01–7.28(8H,m), 7.38(1H,d,J=8 Hz), 7.60(1H,d,J=8 Hz), 8.42(1H,d,J=8 Hz)

EXAMPLE 38

The object compound was obtained according to a similar manner to that of Example 1.

amorphous solid

MASS: 485 (M+1)

$^1$H-NMR (CDCl$_3$) δ: 3.09(3H,s), 3.30–3.50(2H,m), 3.70 (3H,s), 5.62(1H,q,J=8 Hz), 6.70(2H,d,J=8 Hz), 6.99(2H,d,J=8 Hz), 7.01–7.29(6H,m), 7.29–7.40(3H,m), 7.59(1H,d,J=8 Hz), 8.51(1H,d,J=8 Hz)

EXAMPLE 39

The object compound was obtained according to a similar manner to that of Example 1.

amorphous solid

MASS: 485 (M+1)

$^1$H-NMR (CDCl$_3$) δ: 3.10(3H,s), 3.31–3.52(2H,m), 3.70 (3H,s), 5.60–5.72(1H,m), 6.73(2H,d,J=8 Hz), 7.01(2H,d,J=8 Hz), 7.07–7.20(4H,m), 7.20–7.30(2H,m), 7.30–7.50(3H,m), 7.61(1H,d,J=8 Hz), 8.59(1H,d,J=8 Hz)

EXAMPLE 40

The object compound was obtained according to a similar manner to that of Example 1.

amorphous solid

MASS: 469 (M+1)

$^1$H-NMR (CDCl$_3$) δ: 3.08(3H,s), 3.30–3.40(2H,m), 3.71 (3H,s), 5.67(1H,q,J=8 Hz), 6.71(2H,d,J=8 Hz), 7.00(2H,d,J=8 Hz), 7.03–7.30(8H,m), 7.39(7H,d,J=8 Hz), 7.60(1H,d,J=8 Hz), 8.60(1H,d,J=8 Hz)

EXAMPLE 41

The object compound was obtained according to a similar manner to that of Example 1.

mp: 115–118° C.

MASS: 495 (M+1)

$^1$H-NMR (CDCl$_3$) δ: 1.42(3H,t,J=8 Hz), 3.03(3H,s), 3.20–3.31(1H,m), 3.36–3.47(1H,m), 3.70(3H,s), 4.03(2H,q,J=8 Hz), 5.48–5.59(1H,m), 6.73(2H,d,J=8 Hz), 6.90(2H,d,J=8 Hz), 6.99(2H,d,J=8 Hz), 7.00(2H,s), 7.08–7.18(3H,m), 7.23(1H,t,J=8 Hz), 7.39(1H,d,J=8 Hz), 7.61(1H,d,J=8 Hz), 7.86(1H,d,J=8 Hz), 9.60(1H,s)

EXAMPLE 42

The object compound was obtained according to a similar manner to that of Example 1.

mp: >250° C.

MASS: 529 (M+1)

$^1$H-NMR (CDCl$_3$) δ: 3.17–3.40(2H,m), 3.52(3H,s), 3.68 (3H,s), 5.49(1H,q,J=8 Hz), 6.79(2H,d,J=8 Hz), 7.01–7.18 (2H,m), 7.07(1H,s), 7.21(2H,d,J=8 Hz), 7.36(2H,d,J=8 Hz), 7.39(1H,t,J=8 Hz), 7.61(2H,d,J=8 Hz), 8.09(1H,d,J=8 Hz), 8.19(1H,d,J=8 Hz), 8.39(1H,d,J=8 Hz)

EXAMPLE 43

The object compound was obtained according to a similar manner to that of Example 1.

pale yellow amorphous solid

MASS: 571 (M+H)$^+$ $^1$H-NMR (CDCl$_3$) δ: 1.16(3H,t,J=7.0 Hz), 2.79(3H,s), 3.42(1H,dd,J=12.0 and 10.0 Hz), 3.53(1H,dd,J=12.0 and 5.5 Hz), 4.22(2H,q,J=7.0 Hz), 5.53(1H,m), 6.98(1H,d,J=1.0 Hz), 7.04–7.10(4H,m), 7.11(1H,t,J=7.5 Hz), 7.20–7.30(4H,m), 7.33(1H,d,J=7.5 Hz), 7.56(2H,d,J=7.5 Hz), 7.64(1H,d,J=7.5 Hz), 7.91(1H,br d,J=7.5 Hz), 9.21(1H,br s)

EXAMPLE 44

The object compound was obtained according to a similar manner to that of Example 1.

off-white solid mp: 258.5–260° C.

MASS: 421 (M+H)$^+$ $^1$H-NMR (CDCl$_3$) δ: 3.02(3H,s), 3.29(1H,dd,J=13.0 and 8.5 Hz), 3.49(1H,dd,J=13.0 and 5.5 Hz), 5.58(1H,m), 7.02–7.09(3H,m), 7.10(1H,s), 7.15(1H,d,J=7.5 Hz), 7.20–7.43(10H,m), 7.66(1H,d,J=7.5 Hz), 7.73(1H,d,J=7.5 Hz), 9.48(1H,s)

EXAMPLE 45

The object compound was obtained according to a similar manner to that of Example 1.

MASS (ESI) (m/z): 543, 545 (M+H)$^+$ $^1$H-NMR (CDCl$_3$,300 MHz) δ: 1.39(3H,t,J=7 Hz), 3.06 (3H,s), 3.25(1H,dd,J=13 and 9 Hz), 3.41(1H,dd,J=13 and 5 Hz), 3.97(2H,q,J=7 Hz), 5.46–5.61(1H,m), 6.75(2H,d,J=8 Hz), 6.95(2H,d,J=8 Hz), 7.00–7.70(10H,m), 7.90(1H,br d,J=8 Hz), 9.55(1H,br s)

EXAMPLE 46

The object compound was obtained according to a similar manner to that of Example 1.

MASS (ESI) (m/z): 544, 546 (M+H)$^+$ $^1$H-NMR (CDCl$_3$,300 MHz) δ: 1.40(3H,t,J=7 Hz), 3.04 (3H,s), 3.22(1H,dd,J=13 and 9 Hz), 3.41(1H,dd,J=13 and 5 Hz), 3.98(2H,q,J=7 Hz), 5.41–5.55(1H,m), 6.77(2H,d,J=8 Hz), 6.98(2H,d,J=8 Hz), 7.05–7.75(11H,m)

EXAMPLE 47

The object compound was obtained according to a similar manner to that of Example 1.

MASS (ESI) (m/z): 529, 531 (M+H)$^+$ $^1$H-NMR (CDCl$_3$,300 MHz) δ: 3.15(3H,s), 3.29–3.48 (2H,m), 3.81(3H,s), 5.52–5.66(1H,m), 6.91(2H,d,J=8 Hz), 6.97(2H,d,J=8 Hz), 7.00(1H,s), 7.02–7.68(9H,m), 8.01(1H,br d,J=8 Hz), 9.84(1H,br s)

EXAMPLE 48

The object compound was obtained according to a similar manner to that of Example 1.

MASS (ESI) (m/z): 530, 532 (M+H)$^+$ $^1$H-NMR (CDCl$_3$,300 MHz) δ: 3.12(3H,s), 3.25–3.48 (2H,m), 3.82(3H,s), 5.45–5.60(1H,m), 6.93(2H,d,J=8 Hz), 6.99(2H,d,J=8 Hz), 7.03(1H,s), 7.11–7.70(10 H,m)

EXAMPLE 49

The object compound was obtained according to a similar manner to that of Example 1.

MASS (ESI) (m/z). 495 (M+H)$^+$ $^1$H-NMR (CDCl$_3$,300 MHz) δ: 1.39(3H,t,J=7 Hz), 3.02 (3H,s), 3.18–3.48(2H,m), 3.82(3H,s), 3.96(2H,q,J=7 Hz), 5.45–5.59(1H,m), 6.74(2H,d,J=8 Hz), 6.91(2H,d,J=8 Hz), 6.95(2H,d,J=8 Hz), 7.01(1H,s), 7.02–7.68(7H,m), 7.88(1H, br d,J=8 Hz), 9.59(1H,br s)

EXAMPLE 50

The object compound was obtained according to a similar manner to that of Example 1.

MASS (ESI) (m/z): 481 (M+H)$^+$ $^1$H-NMR (CDCl$_3$,300 MHz) δ: 3.04(3H,s), 3.19–3.48 (2H,m), 3.74(3H,s), 3.82(3H,s), 5.47–5.61(1H,m), 6.74(2H, d,J=8 Hz), 6.91(2H,d,J=8 Hz), 6.98(2H,d,J=8 Hz), 7.01(1H, s), 7.02–7.68(7H,m), 7.92(1H,br d,J=8 Hz), 9.66(1H,br s)

We claim:

1. A compound of the formula (I):

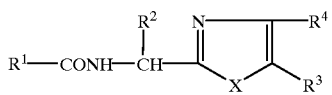
(I)

wherein:

R$^1$ is indolyl or benzonfuranyl;

R$^2$ is lower alkythio(lower)alkyl or a group of the formula:

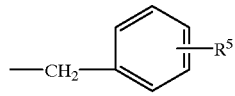

in which R$^5$ is hydrogen, lower alkoxy or halogen;

R$^3$ is hydrogen, quinolyl or phenyl which is optionally substituted;

R$^4$ is hydrogen or optionally esterified carboxy; and

X is NR$^6$, in which R$^6$ is hydrogen, lower alkyl or a group of the formula:

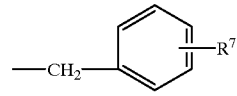

in which R$^7$ is lower alkyl or lower alkoxy, or a pharmaceutically acceptable salt thereof, or a solvate thereof.

2. The compound of claim 1, wherein R$^3$ is quinolyl or phenyl which is optionally substituted by one or more substituents selected from the group consisting of lower alkyl, lower alkoxy, lower alkylthio and halogen.

3. The compound of claim 1, wherein R$^1$ is 2-indolyl or benzofuranyl.

4. The compound of claim 1, wherein R$^3$ is hydrogen.

5. The compound of claim 1, wherein R$^4$ is optionally esterified carboxy.

6. The compound of claim 1, which is a solvate.

7. The compound of claim 6, which solvate is a hydrate.

8. The compound of claim 3, wherein R$^1$ is benzofuranyl.

9. The compound of claim 3, wherein R$^1$ is 2-indolyl.

10. The compound of claim 1, wherein R$^6$ is hydrogen or methyl.

11. The compound of claim 1, wherein R$^3$ is phenyl, chlorophenyl, bromophenyl, fluorophenyl, ethylphenyl or ethoxyphenyl.

12. A pharmaceutical composition, comprising an effective amount of a compound of claim 1, or a pharmaceutically acceptable salt thereof, or a solvate thereof, in admixture with a pharmaceutically acceptable carrier.

13. A method of inhibiting production of nitric oxide in a mammal in need thereof which comprises administering an effective amount of a compound of claim 1 to said mammal.

14. The method of claim 13, wherein said mammal is a human.

15. A method of treating NO-mediated disease in a mammal, which comprises administering an effective amount of a compound of claim 1, to a mammal is used thereof.

16. The method of claim 15, wherein said mammal is a human.

* * * * *

UNITED STATES PATENT AND TRADEMARK OFFICE
CERTIFICATE OF CORRECTION

PATENT NO. : 6,069,162

DATED : May 30, 2000

INVENTOR(S): Itoh et al

It is certified that an error appears in the above-identified patent and that said Letters Patent is hereby corrected as shown below:

Column 105, line 31, "benzonfuranyl" should read --benzofuranyl--.

Column 105, line 32, "alkythio" should read --alkylthio--.

Signed and Sealed this

Twenty-second Day of May, 2001

*Attest:*

NICHOLAS P. GODICI

*Attesting Officer*     Acting Director of the United States Patent and Trademark Office